United States Patent [19]

Kramer et al.

[11] Patent Number: 5,443,848

[45] Date of Patent: * Aug. 22, 1995

[54] HYPERTONIC ISOCHLOREMIC FORMULATIONS FOR TREATMENT OF HYPOVOLEMIC AND CIRCULATORY SHOCK

[75] Inventors: George C. Kramer, Galveston, Tex.; Mauricio Rocha-e-Silva, Sao Paulo; Irineu T. Velasco, S. Paulo, both of Brazil; Charles E. Wade, Sausalito, Calif.

[73] Assignee: Board of Regents, The University of Texas System, Austin, Tex.

[ * ] Notice: The portion of the term of this patent subsequent to Sep. 23, 2010 has been disclaimed.

[21] Appl. No.: 126,242

[22] Filed: Sep. 24, 1993

Related U.S. Application Data

[63] Continuation-in-part of Ser. No. 708,029, May 31, 1991, Pat. No. 5,248,507.

[51] Int. Cl.$^6$ .................... A61K 33/32; A61K 33/26; A61K 33/14; A61K 33/06
[52] U.S. Cl. .................... 424/643; 424/646; 424/680; 424/682; 514/2; 514/23; 514/59; 514/60; 514/557
[58] Field of Search ............... 424/643, 646, 680, 682; 514/2, 23, 59, 60, 557

[56] References Cited

U.S. PATENT DOCUMENTS

| | | | |
|---|---|---|---|
| 3,993,750 | 11/1976 | Fox, Jr. ........................... | 424/128 |
| 4,049,795 | 9/1977 | Laborit .......................... | 424/180 |
| 4,908,350 | 3/1990 | Kramer et al. .................. | 514/2 |
| 4,927,806 | 5/1990 | Kramer et al. .................. | 514/2 |
| 5,248,507 | 9/1993 | e Silva et al. ................... | 424/643 |

OTHER PUBLICATIONS

Excerpt from Advanced Trauma Life Support Instructor Manual, 1989.
Article by Kramer et al., "Small—volume Resuscitation With Hypertonic Saline Dextran Solution," Surgery, vol. 100, No. 2, pp. 239-246, Aug. 1986.
Abstract 21745 by Jan Modig, "Advantages of dextran 70 over Ringer acetate solution in shock treatment and in prevention of adult respiratory distress syndrome: A randomized study in man after traumatic-hemorrhagic shock," Resuscitation 10(4):219-226, 1983.
Article by John B. Cone et al., "Beneficial Effects of a Hypertonic Solution for Resuscitation in the Presence of Acute Hemorrhage," The Am. J. of Surgery, vol. 154, pp. 585-588, Dec. 1987.
Article by M. Rocha e Silva et al., "Hyperosmotic sodium salts reverse severe hemorrhagic shock: other solutes do not," The Am. Physiological Society, pp. H751-H762, 1987.
Abstract #122 by I. T. Velasco et al., "A Comparison of Hyperosmotic and Hyperoncotic Resuscitation from Severe Hemorrhagic Shock in Dogs," Circulatory Shock, vol. 21, No. 4, p. 338, 1987.
Ekblad, H. et al., "Water, Sodium and Acid—Base Balance in Premature Infants: Therapeutical Aspects," Acta P diatrica Scandinavica, 76(1):47-53, 1987.
Smith, G. J. et al., "A Comparison of Several Hypertonic Solutions for Resuscitation of Bled Sheep," Journal of Surgical Research, 39(6):517-528, 1985.
International Search Report, mailed Sep. 4, 1992.

*Primary Examiner*—Raymond Henley, III
*Attorney, Agent, or Firm*—Arnold, White & Durkee

[57] ABSTRACT

The present invention relates to hypertonic crystalloid resuscitation fluids particularly useful in treating hemorrhagic shock. A pharmaceutical formulation prepared and selected ratios of sodium chloride and sodium acetate with a total osmolar concentration exceeding 500 mOsm can be used as a small volume resuscitation fluid which has little effect on plasma chloride levels. Arterial pressure is improved to the point of sustaining oxygen supply to tissues and organs with a significant increase in oxygen delivery and consumption.

25 Claims, 12 Drawing Sheets

HYPERTONIC ISOCHLOREMIC FORMULATIONS FOR TREATMENT OF HYPOVOLEMIC AND CIRCULATORY SHOCK

The United States Government has certain rights to the usage of the present invention pursuant to the terms of Grant No. HL 40296 awarded by the National Institutes of Health.

This is a continuation-in-part application of U.S. Ser. No. 708,029 filed May 31, 1991 now U.S. Pat. No. 5,248,507.

BACKGROUND OF THE INVENTION

1. Field of the Invention

The invention relates generally to hypertonic fluid resuscitation compositions useful for treatment of circulatory and ischemic shock. The composition is a formulation which has particular ratios of sodium acetate/chloride. These formulations provide isochloremic resuscitation and improvements in acid base states which are especially beneficial in cases of large blood loss.

2. Description of Related Art

Circulatory shock is a common life threatening pathophysiological state which occurs secondary to trauma, hemorrhage, burns, sepsis, allergic reactions and heart failure. These different types of circulatory shock are characterized by reduced blood pressure and cardiac output. Furthermore, organ ischemia and inflammation are associated with certain procedures which can result in shock-like microcirculatory abnormalities. Both systemic shock and localized reactions cause a reduction in blood flow and oxygen delivery to vital organs and tissues. This low blood flow condition causes local hypoxia, ischemia, and can lead to loss of cellular and organ function and even death. Accepted definitive treatment for some types of circulatory shock and useful therapy in all types of shock are volume infusions.

The standard of care in initial management of hemorrhagic shock is rapid administration of large volumes of isotonic crystalloid solution, several liters in an adult patient. The preferred fluid is Ringer's lactate, although normal saline or other similar isotonic crystalloid solutions are also used. Recommended continued treatment is based on the observed response to the initial fluid therapy (American College of Surgeons, 1988). As a general rule, guidelines are based on the "three for one" rule. This is based on the long-standing empirical observation that most hemorrhagic shock patients require up to 300 ml of electrolyte solution for each 100 ml of blood lost.

Other isotonic fluid replacement solutions have been used, including isotonic crystalloid solutions mixed with macromolecular solutions of plasma proteins or synthesized molecules with similar oncotic properties (colloids); including albumin, dextran, hetastarch or polygelatin in 0.9% NaCl. Whole blood is also used, but it is expensive, often unavailable, carries some risk of viral infection and cross matching may delay therapy.

Crystalloids and colloids have been used as volume expanders, but generally must be infused in large volume. Such large volumes may cause peripheral and pulmonary edema. Additionally, the large volume requirements of isotonic fluids means that there are time delays and logistic difficulties associated with vascular delivery of effective therapy.

Hyperosmotic crystalloid and hyperosmotic/hyperoncotic (crystalloid/colloid) formulations offer some physiological benefits for the treatment of circulatory shock, including improved efficacy for restoration of overall cardiovascular function in animals and man compared to conventional resuscitation (Cone et al., 1987). Normalization of circulatory function has been obtained with such solutions (Kramer and Holcroft, 1990). Small volumes of salt/concentrated dextran formulations have been shown to rapidly restore and sustain normalization of circulatory function in hemorrhage (Kramer et al., 1986; Velasco et al., 1987). However, there remain some important limitations/side effects.

Small volume resuscitation of hypovolemic hemorrhage shock using 7.5 % NaCl solution (Nakayama et al., 1986; Bitterman et al., 1987; Muir et al., 1987) and a combination of 7.5 % NaCl and 6% Dextran-70 (Kramer et al., 1989 and 1990; Kreimeir et al., 1987, Velasco, et al., 1989) has been extensively studied. These studies have shown that HSD treatment results in a rapid improvement of blood pressure and near normalization of cardiac output, vital organ perfusion and $O_2$ delivery when administered in volumes of 4-6 ml/kg to animals hemorrhaged 35-50 ml/kg. However, in patients with internal injury, pre-hospital resuscitation before surgical intervention may lead to increased bleeding as rapid rises in blood pressure re-open clotted and tamponaded vascular injuries. This phenomenon in uncontrolled hemorrhage has been demonstrated in different animals models in which mortality was increased subsequent to resuscitating with small volumes of HSD or large volumes of LRS (Bickell et al., 1991; Gross et al., 1988). The possibility that aggressive pre-hospital field resuscitation is more harmful than helpful has motivated recent trials in which all volume support is delayed until the start of surgery (Mattox et al. 1992).

In a recent examination of patients treated with either 7.5 % NaCl or LRS in the emergency room, no untoward effects on bleeding, neurological outcome, or cross-matching of blood were found, and there were no incidents of central pontine myelinosis (Vassar et al. 1990). There was, however, a significant hyperchloremic acidosis in 8 out of the 58 patients given HSD. While the acidemia in this study was attributed to the patients' pre-existing morbidity, a rapid decrease of pH in an already acidotic shock state could result in cardiac dysfunction (Onarheim et al., 1990; Walsch et al., 1991). Additionally, it was consistently found that a 4-6 ml/kg infusion of HSD in shocked animals was followed by an immediate decrease in pH of nearly 0.1 pH units (Kramer et al., 1986).

Hypertonic saline infusions in shocked animals and patients have been shown to cause an initial acidosis and hypokalemia. Treatment with hypertonic saline can also lead to a hyperchloremic acidosis, possibly due to excessive chloride load. Some isotonic Ringers solutions and mildly hypertonic formulations mimic sodium and chloride concentration ratios found in plasma and are thought to decrease the likelihood of acidosis (Fox, 1976). Circulatory shock is often associated with an acidosis and thus increased acidotic insult may be deleterious.

Although hypertonic saline rapidly improves both blood pressure and cardiac output, these beneficial effects may be overshadowed by deleterious effects from increased blood pressure. Uncontrolled internal bleeding in trauma patients may be aggravated by increased pressure, leading to increased bleeding. Return of normal blood pressure resulting in increased bleeding due to arterial pressure increase may lead to increased mortality over no treatment. Therefore, ideal pre-hospital resuscitation would increase cardiac output but only modestly increase blood pressure.

Another aspect of resuscitation fluids is their use under less than ideal (non hospital) conditions. Logistic restraints may severely curtail transportation of weighty or voluminous material. In battlefield situations it may be impractical to administer large volumes, yet there is a critical need to rapidly restore oxygen delivery to critical organs and to prevent or reverse the effects of traumatic shock.

SUMMARY OF THE INVENTION

The present invention addresses one or more of the foregoing problems and particularly addresses some of the drawbacks associated with administration of currently used isotonic and hypertonic resuscitation fluids, particularly in the treatment of circulatory shock. The invention generally relates to hypertonic crystalloid pharmaceutical compositions that include specific ratios of sodium acetate and sodium chloride.

It has been discovered that particular compositions are unexpectedly useful for small volume rapid restoration of oxygen consumption and oxygen delivery in severely hemorrhagic individuals. The compositions have strong buffer capacity that rapidly normalize metabolic acidosis and are capable of restoring adequate blood flow to organs and tissues while maintaining arterial blood pressure at a level just sufficient to maintain blood flow to the recumbent mammal. Beneficial effects from administration are obtained rapidly, resulting in large increases in cardiac output and oxygen delivery to tissues. Consequences are increased arterial pressure minimally compatible with maintenance of adequate blood supply to body organs and tissues while minimizing increased blood loss associated with higher increases in arterial pressure.

The inventors have discovered that pharmaceutical compositions comprising sodium chloride/acetate unexpectedly maintain plasma chloride levels and prevent hyperchloremic acidosis when administered as a small volume resuscitation fluid. Isochloremic resuscitation is achieved only when sodium chloride/acetate are present in certain relative concentrations, that is, about 2 to 7 osmolar parts sodium acetate and about 1-3 osmolar parts sodium chloride, preferably at 5:3 or 7:1 and most preferably at 6 molar pans of NaAc to 2 parts of NaCl. In these relative osmolar concentration ranges, administration of the combined salt solution results in little, if any, change in the plasma chloride concentration. In a preferred embodiment, sodium acetate to sodium chloride ratio is approximately 6:2 osmolar pans in a solution with a total osmolarity of about 2400 mOsm parts. Surprisingly, these particular ratios of acetate/chloride combined with a colloid such as dextran in a resuscitation solution are remarkably effective in rapidly increasing oxygen delivery and oxygen function in severely hemorrhaged mammals.

The role that the dextran component plays in small volume resuscitation with hyperosmotic/hypertonic solutions is well defined (Smith, et al., 1985; Kramer and Walsh, 1991; Wade, 1990). The hyperosmotic crystalloid component rapidly causes fluid to osmotically repartition from the cellular space into the vascular space. Direct comparisons of 2400 mOsm/L NaCl alone versus 2400 mOsm/L NaCl/6%-Dextran show a slightly better initial plasma volume expansion and, more importantly, a much more sustained response and higher survival rates. In the present studies hyperosmotic crystalloid solutions of sodium acetate-sodium chloride compositions with (Example 2) and without dextran were examined. Different hyperosmotic crystalloids such as NaCl, sodium chloride:sodium acetate, all combined with 6%-Dextran were compared. It is clear from a comparison of physiological data of these different groups that it is the sodium chloride:sodium acetate hyperosmotic crystalloid component that imparts the physiological benefit of the invention, i.e., isochloremia, higher cardiac outputs, smaller increases in blood pressure, better acid-base balance, and higher oxygen delivery and consumption. A hyperosmotic crystalloid consisting of about 6 molar parts sodium acetate and 2 molar parts sodium chloride would offer physiologic benefit even without the dextran component.

As used herein, the term mOsm/L expresses milliosmoles per liter of solution. Osmolarity of a solution is a colligative property determined by the pressure differential across a semipermeable membrane, e.g., a cell wall, engendered by a solvent and any dilute solution. The osmotic pressure of the dilute solution depends on the number of particles in solution, not on weight or type of solute. A mole of monovalent salt thus provides 2 osmoles whereas a mole of sugar which is un-ionized and does not dissociate provides 1 osmole. An osmole of solute in a liter of solution is a 1 osmolar solution. An osmole of solute added to 1 kilogram of water is a 1 osmolal solution. Generally this distinction and slight difference in actual concentration is of little significance.

Three general formulations of crystalloid/colloid solutions have been examined. These include HSD solutions which are 2400 mOsm/L 7.5% NaCl and 6% dextran70. HAD solutions are those which are also 2400 mOsm/L and include sodium chloride and sodium acetate in several different ratios in 6% dextran70. HA solutions contain only the 2400 mOsm/L sodium acetate and sodium chloride alone. The LR or LRS solutions are those that contain isotonic sodium chloride/lactate solutions and are the current standard of care resuscitation solutions. The particular ratio of acetate/chloride employed in the various compositions is specified.

The new pharmaceutical compositions with specific sodium acetate/chloride ratios typically induce a large increase in cardiac output with a modest rise in arterial blood pressure almost immediately upon administration. The rise is sufficient to maintain blood perfusion to essential body organs and to tissues while the transfusion recipient is in a recumbent position. Generally, the rise in arterial blood pressure will not be sufficient to maintain adequate blood profusion to body tissues if the subject is in an upright position. This finding was quite surprising because in general, increased blood flow after resuscitation will be accompanied by significant rise in arterial pressure. Such increases in arterial pressure are often considered detrimental because of increased arterial bleeding which is particularly detrimental in cases of severe hypovolemia. Often the increased internal loss of blood is not compensated by administration of commonly used resuscitation fluids and fatal shock may ensue. Furthermore, even if additional fluid is given to correct volume, the increased bleeding results in loss of red blood cells and lower oxygen carrying capacity.

Isotonic saline and hypertonic saline typically promote increased blood flow to body organs and tissues but the pressure rise is significantly higher than that observed with the pharmaceutical composition discovered by the inventors.

Typically, the pharmaceutical composition of the present invention will have a total osmolar concentration in excess of 500 mOsm. For general purposes, these solutions will be ideally around 2400 mOsm. The high osmolarity of the solution provides an effective fluid expander, thus fluid is pulled across cell membranes and the capillary wall. Water is redistributed through the interstitial and vascular spaces. High osmolarities result in rapid volume expansion, arteriolar vasodilation and increased contractility. Together, these changes cause an increase in cardiac output and oxygen delivery to tissues.

An unexpected aspect of the invention is an ability to provide increased blood flow to essential organs without causing an undue increase in arterial pressure. While 50:50 mixtures of sodium acetate:sodium chloride will enhance cardiac output and not unduly increase arterial pressures, such combinations are not isochloremic. Alternatively, pure hypertonic acetate mixtures cause hypochloremia and are not superior to hypertonic saline (Rocha e Silva et al., 1987). The new formulations are particularly valuable in preventing possible acidosis due to excess chloride ion precisely because they cause little alteration in plasma chloride levels.

Several modifications of the pharmaceutical composition are possible; for example, a colloid or a crystalloid may be added to the hypertonic sodium acetate/sodium chloride. Suitable colloids may include dextran soluble starches, gelatins and proteins. An example of the soluble starch is hydroxyethyl starch. Varying amounts of crystalloids could also be added, for example, glucose, amino acids, magnesium salts, potassium salts and salts with appropriate anions having buffering capacity. However, it will be appreciated that while inclusion of colloids which have high molecular weights will have little effect on total osmolarity, low molecular weight species such as salts or amino acids may add significantly to total osmolarity. This is a consideration in preparing formulations for particular use. Additionally, other components may be added, for example, certain types of anti-shock drugs such as fructose diphosphate or ATP and $Mg^{++}$, as well as oxygen radical scavengers, deferoxamine compounds, neutrophil adherence inhibitors, leukotriene blockers, thromboxane blockers, calcium channel blockers and the like.

Additionally, a specific colloid of special benefit would be stroma free hemoglobin. The addition of stroma-free hemoglobin or oxygen carrying fluorocarbons to the pharmaceutical composition would provide a formulation to increase both blood flow and the oxygen carrying capacity of blood. These two factors would have a multiplier effect on oxygen delivery.

A solution of hypertonic sodium chloride and sodium acetate in combination with stroma-free hemoglobin is contemplated as a particularly useful embodiment of the invention. Stroma-free hemoglobin solutions are useful for the treatment of shock in that they have oncotic properties and when infused into a shocked animal increase blood volume, blood flow and oxygen carrying capacity and thus increase oxygen delivery to tissues (Rosen, et at., 1982).

On the other hand, stroma-free hemoglobin also is a vasoconstrictor which can impede tissue blood flow and increase the work required of the heart. The strong vasodilatory properties of specific ratios of sodium acetate and sodium chloride coupled with the augmentation of oxygen utilization provided by such solutions suggests that a hypertonic sodium chloride/sodium acetate/hemoglobin formulation would eliminate the vasoconstrictor effects of hemoglobin and have additive and synergistic beneficial effects.

In this connection, the inventors have made the surprising discovery that oxygen delivery and function are rapidly attained with formulations of limited ratios of NaCl/NaAc and are especially beneficial when included in a formulation with about 6% dextran. While the importance of the addition of the hypertonic dextran or other colloid is established (Walsh and Kramer, 1991) the unique and unexpected physiological benefit of the invention comes from the limited ratios of hyperosmotic sodium acetate and sodium chloride. The hypertonic formulations greatly increase cardiac output with minimal increases in blood pressure; provide near isochloremic resuscitation and unexpectedly increase oxygen delivery, particularly oxygen consumption.

Yet another aspect of the invention is a method of providing intravascular support, generally to those patients suffering generally from circulatory shock caused by loss of blood, for example, or burn, sepsis, allergic reaction, heart failure or hemorrhage. The novel resuscitation fluid is a combination of sodium acetate and sodium chloride with a ratio of about 1–2 osmolar parts of sodium chloride and 2–7 osmolar parts of sodium acetate and a total osmolar concentration of at least 500 and preferably 2400 mOsm per liter. Although fluid replacement is possible through oral administration, the method is slow and relatively ineffective.

The patient is administered an effective amount of a pharmaceutical composition having approximate ratios of 7:1, 5:3 or 6:2 osmolar parts of sodium acetate and sodium chloride respectively with a total osmolarity of at least 500 mOsm/L. The amount will depend somewhat on the medical situation, the physiological state of the recipient and the total osmolarity of the solution employed. Administration is intravascular, preferably intravenous or intraosseous. A 2400 mOsm composition is preferably administered in a dose of about 4–8 ml/kg over a period of a few minutes in critical shock or up to 3 hours for less critical but longer term circulatory support. A 500 mosm formulation would be administered in a dose of 20 to 40 ml/kg up to several hours to maintain good circulatory function, acid-base balance and overall metabolic function.

Generally, fluid resuscitation is required under conditions of hypovolemia. Severe hypovolemia may result from a variety of insults, including surgeries such as orthopedic surgery. Massive blood loss may occur from surgeries necessary to repair or remove damaged liver, esophagus or other tissues and organs.

The most common types of circulatory shock result from hemorrhaging or loss of blood through external or internal bleeding. Blood loss may be especially large in severe arterial bleeding, which may occur after a large artery or arteries are cut in lesions such as in traumatic accidents. Often in these cases, there is an initial rapid blood loss and potential for sustained blood loss depending on the dimensions of the arterial lesions. Blood is lost at a variable rate which is proportional to the driving or arterial pressure.

All types of circulatory shock are characterized by reduced blood pressure and cardiac output with the resultant reduction in blood flow and oxygen delivery to vital organs and tissue. Low flow causes local hypoxia, ischemia, possibly leading to loss of cellular and organ function and ultimately death. The goal of resuscitation is to repair this cardiovascular deficit by restoring blood flow and oxygen delivery. This normally restores blood pressure as well, but the increased blood pressure leads to an increase in internal blood loss which may lead to shock and death. In this respect the invention is of particular value in that it restores blood flow and oxygen delivery without large and rapid increases in blood pressure.

Prepackaged formulations comprising the novel isochloremic pharmaceutical compositions are also contemplated as part of the present invention. Generally, one will desire to package the disclosed chloride/acetate/dextran hypertonic formulations in containers such as glass bottles, plastic bottles or bags, tubes, or, where shipping to a central location is requested, in sterile carboys from which desired volumes may be metered automatically or hand dispensed.

A convenient form of prepacking is in elongated bags or in a shape convenient for hand manipulation. Optionally containers, particularly those designed for individual administration, may be pressurized, allowing for automatic delivery when appropriately inserted for intravenous or intraosseous administration. A commercially available infusor may be obtained from Baxter is the Intermate ® LV 250. This product is made from an elastomeric membrane enclosed in a hard shell which when hooked up to a patient dispenses fluid at a controlled, measured rate.

Intravenous administration requires a needle and tubing, which is often conveniently available in kits containing components such as Baxter Basic Solution Set Flashball ®, Device, 16 gauge Bad ® one piece IV placement unit, and materials to prep the insertion site such as Baxter Cepti Seal IV prep kit. Similar kits could be made available for intraosseous access. These typically include special spinal needles and suitable tubing.

Other components intended for convenience and specialized use may be included with prepackaged formulations of the new resuscitation fluid. Such components, as discussed, include various accessory equipment or appurtenances which may be collectively referred to as paraphernalia and which is intended to include the equipment herein described.

DETAILED DESCRIPTION OF THE PREFERRED EMBODIMENTS

Figure 1:
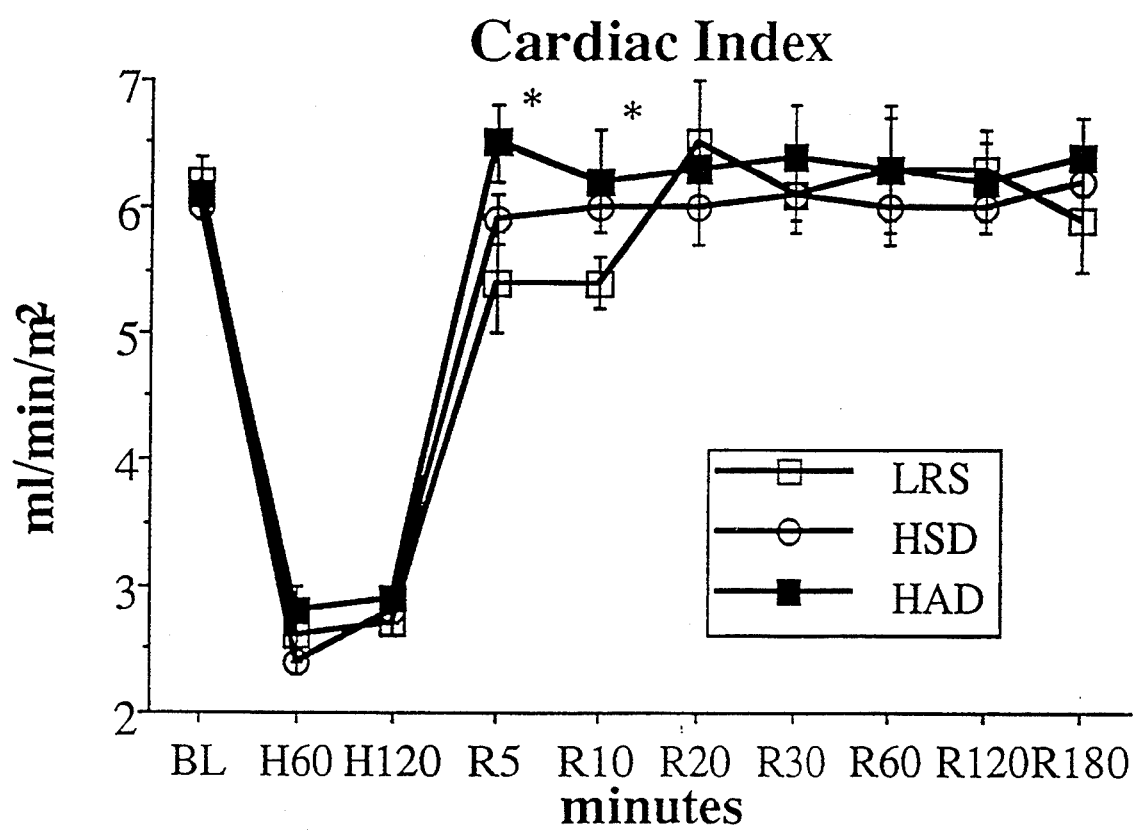
FIG. 1. Cardiac index in conscious sheep during baseline and hemorrhage, and following resuscitation. By experimental design, all three groups (LRS, HSD and HAD) were resuscitated to and maintained at baseline cardiac index. Higher $DO_2$ were observed with HAD compared to both LRS and HSD. Values represent the mean±SEM. *=$P<0.05$ LRS vs HAD; #=$P<0.05$ HSD vs HAD.

The described work undertook a comparison of various hemodynamic and metabolic effects with various combinations of sodium chloride and sodium acetate in a isochloremic hypertonic 2400 mOsm/L solution for shock resuscitation. Five different hypertonic sodium chloride or chloride/acetate formulations were tested: acetate alone; acetate/chloride ratios of 7:1, 6:2 and 5:3; and chloride. All formulations included 6% dextran. The chloride formulation was the classic resuscitation solution of dextran and 7.5% NaCl.

The results describes were based on randomized, double blind treatment protocols. Experiments were performed on sheep, dogs and pigs, all with substantially similar results. Typical experiments involved bleeding morphine-pentobarbital anesthetized dogs at 40 mL/kg over a period of 30 min, then treating with a coded formulation. The formulation was administered to dogs in a volume of 4 mL/kg within 4 min, from 30-40 min after start of bleeding. Measurements of arterial pressure, cardiac output, blood gases, plasma $Na^+$ and $Cl^-$ were measured before the start of bleeding, before and at 5 min intervals, for 60 min after treatment. Oxygen consumption ($VO_2$) was estimated from cardiac output and arteriovenous oxygen differences.

Generally, the results showed that solutions 7:1, 6:2 and 5:3 best fit the description of isochloremic formulation with negligible effect on plasma $Cl^-$. The pure acetate solution induced hypochloremia because of the induced osmotic transcapillary movement of fluid from the cellular space into the vascular space. Isochloremic sodium acetate/sodium chloride solutions given after severe blood loss (40 mL/kg blood volume deficit) induce a smaller pressor, but larger cardiac output response, in comparison with the pure chloride solution. Isochloremic solutions significantly increase oxygen consumption and restore acid base equilibrium. The pure chloride solution induced a smaller oxygen consumption recovery and induced a transient hyperchloremic acidosis.

The goal of pre-hospital resuscitation is to improve oxygen delivery and oxygen consumption rather than to simply increase blood pressure. The data presented herein show that even though resuscitation with HAD achieved the pre-morbid cardiac output, the blood pressure was significantly lower than with HSD and LRS. This suggests that HAD is a more appropriate treatment for instances of high blood loss, particularly when there is a continued risk of internal hemorrhage. Of at least equal importance, the oxygen delivery with the HAD group was significantly better than the other two groups. In addition the oxygen consumption returned to baseline indicating that the resuscitation was successful in bringing the oxygen consumption back to the independent portion of the oxygen delivery/consumption curve.

The invention concerns a hypertonic crystalloid resuscitation fluid containing specified amounts of sodium chloride and sodium acetate. Unexpectedly, the particular salt combination used as a pharmaceutical formulation has little effect on plasma chloride concentrations when administered to subjects in circulatory shock despite the infused solution itself having a chloride concentration of 208 mEq/L in the 6:2 molar ratio embodiment. In addition to its isochloremic properties as a resuscitation fluid, the pharmaceutical composition discovered by the inventors provides a substantial increase in blood flow to tissues and organs while unexpectedly eliciting less of a rise in arterial pressure than other sodium-containing resuscitation solutions. The surprisingly minimal arterial pressure rise is sufficient to maintain blood flow to critical organs while the subject is in a recumbent position but has the effect of minimizing internal bleeding in situations where such bleeding may be the cause of the shock. Additionally, the formulation increases oxygen consumption to an unexpected and superior degree compared to hypertonic saline formulations.

There are several cardiovascular mechanisms that contribute to the effectiveness of HAD as a small volume resuscitation. The primary mechanism appears to be a rapid vascular volume expansion by osmotically induced fluid shifts from the cellular space into circulation secondary to the hypertonic NaCl with the hyperoncotic Dextran (Kramer et al., 1989; Smith et al., 1985; Lopes et al., 1981). A contributing mechanism is thought to be the hyperosmolality induced positive inotropic and chronotropic stimulation of the heart and dilation of arterioles (Kien et al., 1989; Wildenthal et al., 1969; Gazitua et al., 1971). Because HAD is a better vasodilator than HSD, the increased contractility combined with a reduced afterload results in rapid improvement in cardiac output at a relatively low blood pressure and less cardiac work. This may be particularly important in patients who need volume support and who have pre-existing cardiac dysfunction.

Additionally and perhaps more important is that HAD provides metabolic advantages over HSD. HAD has a strong buffer capacity that rapidly normalizes the metabolic acidosis. Normalized pH optimizes enzymatic and cellular metabolic activities and function (Guyton 1991). Also a more alkaline pH shifts the oxygen hemoglobin dissociation curve to the left (Guyton 1991) allowing a higher loading of oxygen by hemoglobin in arterial blood and subsequently a better oxygen delivery. On the other hand, the left shift in the oxygen hemoglobin dissociation curve would be expected to hinder oxygen unloading in the tissues. Results of experiments in two species, sheep and dog, herein described show that there is less difference in oxygen consumption than oxygen delivery, but HAD demonstrated higher mean levels of oxygen consumption at all time points measured. Thus, although unloading may be affected overall, improved $O_2$ delivery with HAD resulted in better oxygen consumption. This may ultimately be the single strongest rational for the use of HAD in trauma resuscitation. The higher oxygen delivery observed in the HAD groups appeared to be due to a combination of three factors: 1) higher cardiac indices, 2) slightly higher hemoglobin values and 3) greater $O_2$ binding to hemoglobin in arterial blood.

The novel pharmaceutical formulation is amenable to modification according to medical need; for example, in routine hospital procedures requiring fluid replacement or enhancement or in special situations, such as the need for immediate emergency medical care in isolated geographical areas. In critical situations, aggressive resuscitation with conventional resuscitation fluids frequently causes increased internal bleeding and hyperosmotic crystalloid solutions such as sodium chloride may also induce acidosis. Both these disadvantages are overcome by using the new isochloremic formulation.

MATERIALS AND METHODS

Animal Care and Use

The experimental protocols described herein were approved by the Animal Care and Use Committee of the University of Texas Medical Branch with strict adherence to ACUC guidelines regarding humane use of animals. The experimental protocols for dogs were approved by the Ethics Committee of the Instituto do Corocao and conform to NIH guidelines for the use of animals.

Surgical Preparation

Sheep were prepared for conscious hemorrhage and resuscitation experiment. After an overnight fast the animals were anesthetized with 1 to 3% Halothane and aseptically prepared with catheters (Model 93A-13 1-7F, Edwards Laboratories, Anasco, PR) in the femoral artery, the femoral vein and the pulmonary artery. After a retroperitoneal incision was made in the left flank, the distal abdominal aorta was identified and a transit time ultrasonic flow probe (8 or 10 mm, Transonic Systems Inc. Ithaca, N.Y.) was placed around it. The flow probe was fixed to the psoas muscle to prevent rotation. Animals were given 5-7 days to recover from the surgical procedure before experiments began.

Systemic hemodynamics and blood gas measurements

Mean aortic pressure (MAP) and central venous pressure (CVP) were measured using transducers (P23ID Statham Gould, Oxnard, Calif.) connected to catheters adapted with continuous flushing devices. Pressures were monitored on an Electronic Medicine Honeywell Recorder (Model OM-9) with graphic and digital display. A horizontal plane through the olecranon joint on the front leg of the animal was taken as the zero reference point for blood pressure. Cardiac output was determined by the thermal dilution technique utilizing a cardiac output computer (Model 9520 American Edwards Laboratory, Irvine, Calif.). Arterial and mixed venous blood gas were measured with a blood gas analyzer (System 1303, Instrumentation Laboratory, Inc. Cidra, PR), corrected to the animals temperature. Arterial ($SaO_2$) and mixed venous oxygen saturations were determined with a Co-Oximeter (Model 282, Instrumentation Laboratory, Inc., Cidra, PR). Aortic abdominal blood flow was measured with transit time ultrasonic flow probes connected to the T 101 ultrasonic flow meter (Transonic Systems Inc., Ithaca, N.Y.). Total oxygen consumption was calculated as the cardiac output times the difference in arterial-venous oxygen content. Serum and urine concentrations of $Na^+$, $K^+$ and $Cl^-$ as well as total osmolality were measured by ion electrode analyzer and freezing point depression.

Experimental Design

Water was withheld from the animals for 24 hours prior to each experiment, while free access to food was provided. This slightly dehydrated the sheep, but made a more reliable and reproducible model of hemorrhagic hypovolemia. All animals tolerate the hypotension and resuscitation procedure well and were used in 3 experiments, one for each solution, with a minimum of 7 days between experiments. This procedure was found in previous studies (Kramer, et al., 1986; Smith, et al., 1985) to produce the most reproducible and sensitive model to evaluate different fluid regimes.

A Foley catheter was inserted on the day of the experiment. The study order for three solutions was randomly assigned and solutions were placed in coded bag with treatment "blinded" to the investigator and the technician performing the study.

The three solutions used for resuscitation were: 1) standard isotonic 274 mOsml/L Lactated Ringers. (LRS), 2) 2400 mOsmol/L 7.5% NaCl/6% Dextran 70 (HSD), and 3) 2400 mOsmol/L hypertonic NaCl acetate/dextran (HAD), which consists of 3 molar parts Na-acetate to 1 molar part NaCl and 6% Dextran 70.

An initial 2-hr baseline period, during which hemodynamics and blood were obtained, was followed by a 2-hr period of hemorrhagic hypotension. The animals were bled via the venous catheter to lower their mean arterial pressure to 50 mmHg in 15 min. Mean arterial pressure was maintained at this level±mmHg for 2 hrs by additional bleeding as necessary. Although this significant level of hemorrhage caused substantial reductions in oxygen delivery and consumption with increases in lactate, animals remained conscious but lethargic and relaxed and without any apparent pain similar to simple hemorrhage in man. Blood was collected and stored in ACD collection bags. At the end of the 2 hr hemorrhage period, each sheep was treated with a venous infusion of the resuscitation solution with volume delivered over a 3 hr period as needed to restore and maintain cardiac output at baseline. A continuous readout of aortic blood flow was used as an index of cardiac output, allowing quick adjustment of infusion rates as needed. By resuscitating to a clear physiological endpoint, these experiments were designed to establish the needed dose to determine efficacy of HAD, HSD and LR for normalization of cardiovascular function. At the end of the 3 hr resuscitation period, data collection was discontinued, all shed blood was returned, and the animals were then allowed free access to food and water.

Statistical Analysis

Analysis of co-variance adjusted for repeated measures were used to determine significant differences between the 3 solution groups. If differences were found, then the paired Student's t-test with Bonferroni correction for numbers of corrections between the individual groups was used. Differences between groups were tested at baseline, after 60 and 120 min of hemorrhage and at 5, 10, 20, 30, 60, 120 and 180 min after resuscitation started. Differences were considered significant if $P<0.05$. All data shown are expressed as mean±standard error of the mean.

The following examples illustrate preferred embodiments of the practice of the invention. It should be understood that these examples are intended to be illustrative of the invention and in no way limiting.

EXAMPLE 1

This experiment illustrates the differences between two small volume resuscitation formulations, the HSD and the HAD formulation, and a "standard of care" Ringers lactate solution which is used in large volume. Both HSD and HAD contain dextran and sodium chloride, but HAD also contains sodium acetate. Results show that both HSD and HAD reduce early volume requirement for resuscitation to less than 10% of Ringers lactate, but only HAD showed a high flow/low pressure resuscitation that potentially reduces internal bleeding in uncontrolled hemorrhage during resuscitation. HAD did not elevate chloride levels, had better buffer capacity, and rapidly normalized pH. HAD provided better $O_2$ delivery and consumption for the same cardiac output. The results highlight the superiority of HAD to both isotonic Lactate ringers and HSD formulations.

Comparison of LRS, HSD and HAD

Three groups of sheep were tested under the protocol previously herein described under Materials and Methods.

Figure 2:
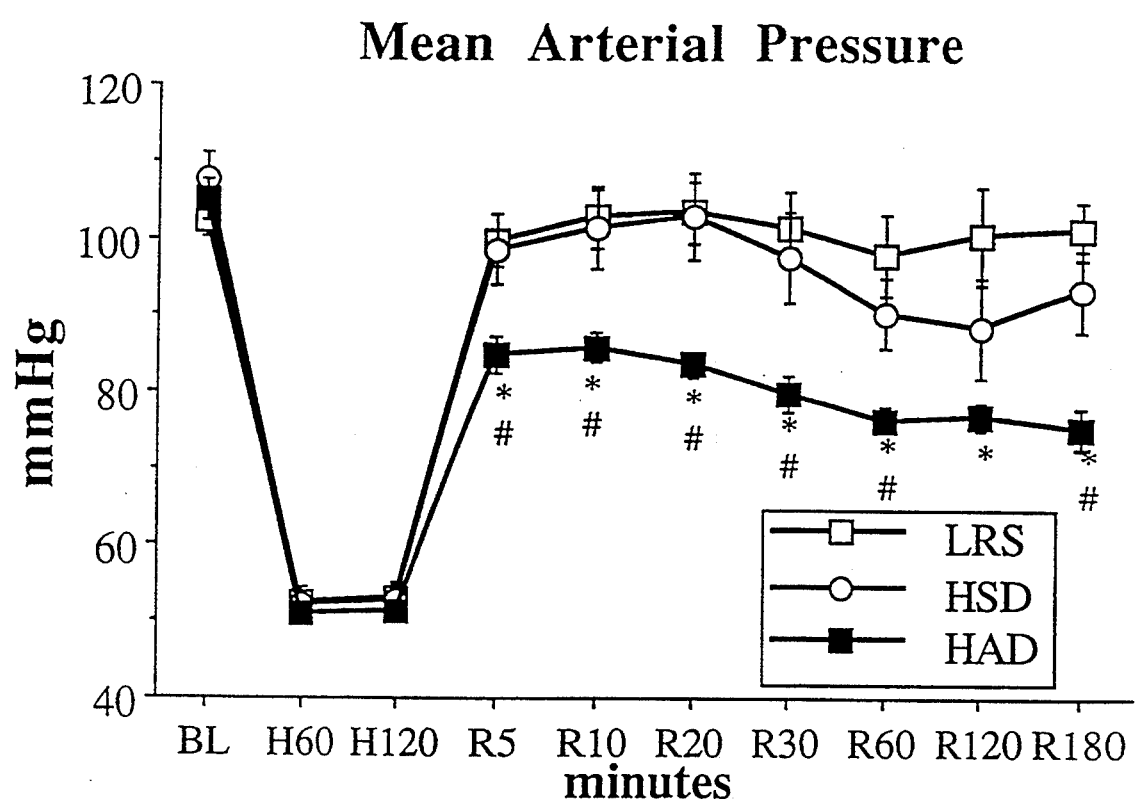
FIG. 2. Mean arterial pressure (MAP) during baseline, hemorrhage and following fluid resuscitation using LRS, HSD and HAD in conscious sheep is shown. Despite equivalent cardiac indices, blood pressure was lower with HAD. Values represent the mean ±SEM. *=$P<0.05$ LRS vs HAD; #=$P<0.05$ HSD vs HAD.

Baseline and hemorrhage values of mean arterial pressure and cardiac index were not statistically different for the three groups (FIGS. 1 and 2). Lowering mean arterial pressure to 50 mmHg during the first 30 min of the hemorrhage period required removal of 25-30 ml/kg of blood. This level of hypotension was maintained for the duration of the 2 hr hemorrhage period by removal of additional blood as necessary. In the 18 experiments, the sheep were bled a total of $42\pm3$ ml/kg: $1740\pm91$ ml (LRS), $1759\pm160$ ml (HSD) and $1785\pm58$ ml (HAD) over the entire 2 hr hemorrhage period. This represents about two-thirds of the sheep's estimated blood volume. Average baseline values of cardiac index ranged from 5.9 to 6.3 L/min/m$^2$ (FIG. 1). During hemorrhage, cardiac index decreased to less than 50% of baseline with values ranging from 2.5 to 3.0 L/min/m$^2$. Thus by most clinical measures, these animals were subjected to moderate to severe hemorrhage shock.

By experimental design, the animals were resuscitated to the same physiologic endpoint of baseline cardiac index and maintained there with the resuscitative fluid as needed for 3 hours (FIG. 2). Cardiac index returned to baseline at 5 min. in HSD and HAD groups and by 20 minutes in the LR group. This lag was due to the time required to infuse the large amount of LR needed. With all three groups, as resuscitation continued, the animals would stand and become more active compared with their previous lethargic state. Cardiac indices were well maintained in all three groups thereafter. On the other hand, MAP was significantly lower by nearly 20 mmHg with HAD than with LRS or HSD throughout the 3 hrs of resuscitation.

Figure 3:
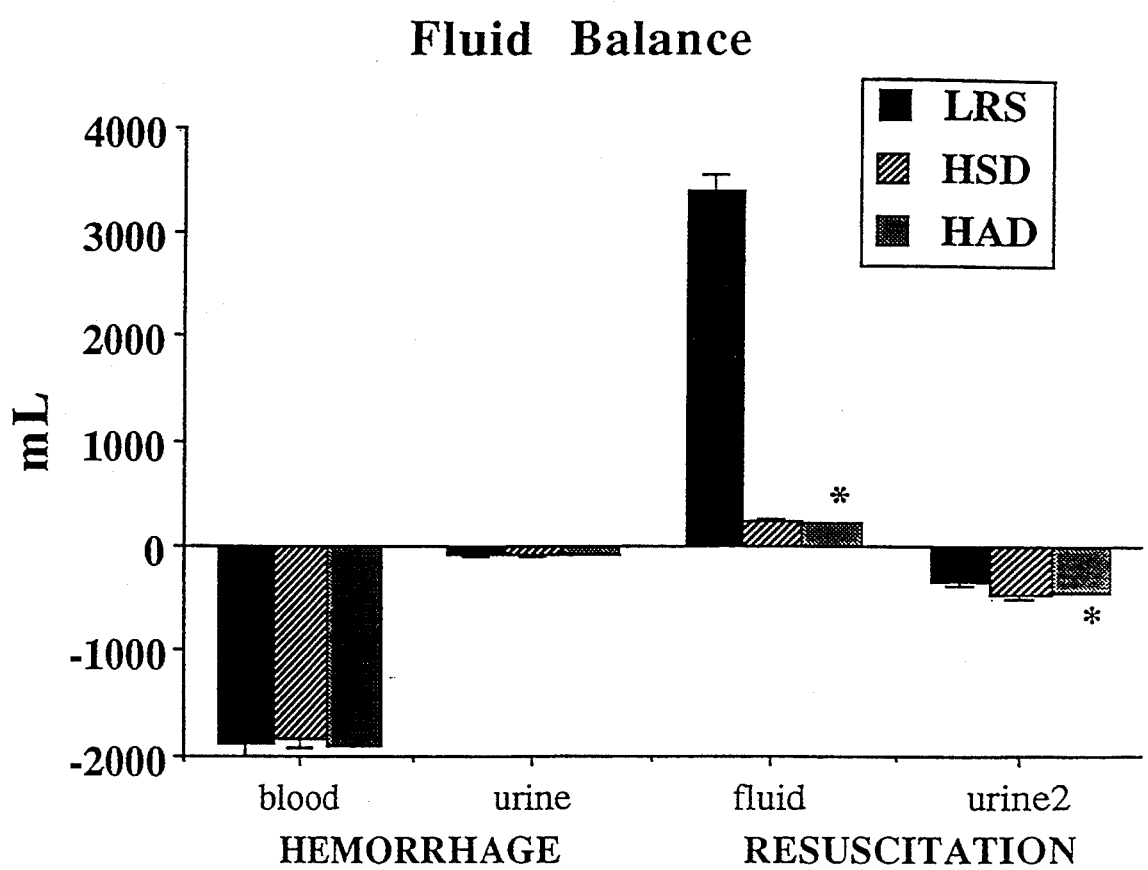
FIG. 3. Mean fluid balances±SEM during hemorrhage and following resuscitation is shown. In the 18 experiments, the sheep were bled 1740±91 ml (LRS), 1759±160 ml (HSD) and 1785±58 ml (HAD) over the entire 2 hr hemorrhage period. The amount of resuscitative fluid required to maintain each group at baseline cardiac index for 3 hrs of resuscitation are: LRS=3463±234 ml, HSD=244±39 ml, and HAD=236±29 mi. The urine output was also significantly higher in the HSD and the HAD groups than LRS group. No differences were noted between HSD and HAD in any volume measurements. *=$P<0.05$ LRS vs HAD; #=$P<0.05$ HSD vs HAD.

The amount of resuscitative fluid required to maintain each group at baseline cardiac index for 3 hrs of resuscitation is shown: (FIG. 3) LRS=$3463\pm234$ ml, HSD=$244\pm39$ ml, and HAD=$236\pm29$ mi. The urine output was also significantly higher in the HSD and the HAD groups than LRS group. No differences were noted between HSD and HAD in either volume infused or urine output.

Figure 4:
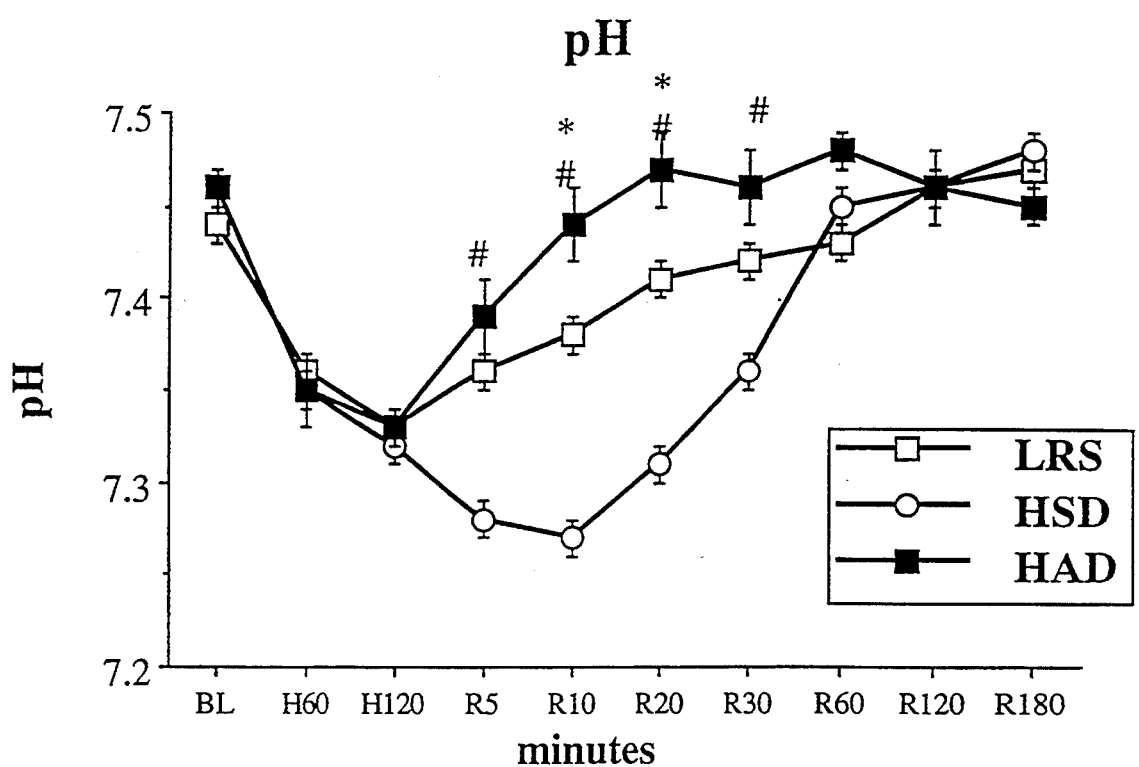
FIG. 4. Arterial pH during baseline and hemorrhage, and following resuscitation is shown. Arterial pH was more rapidly normalized with HAD. Values represent the mean±SEM. *=$P<0.05$ LRS vs HAD; #=$P<0.05$ HSD vs HAD.
Figure 5:
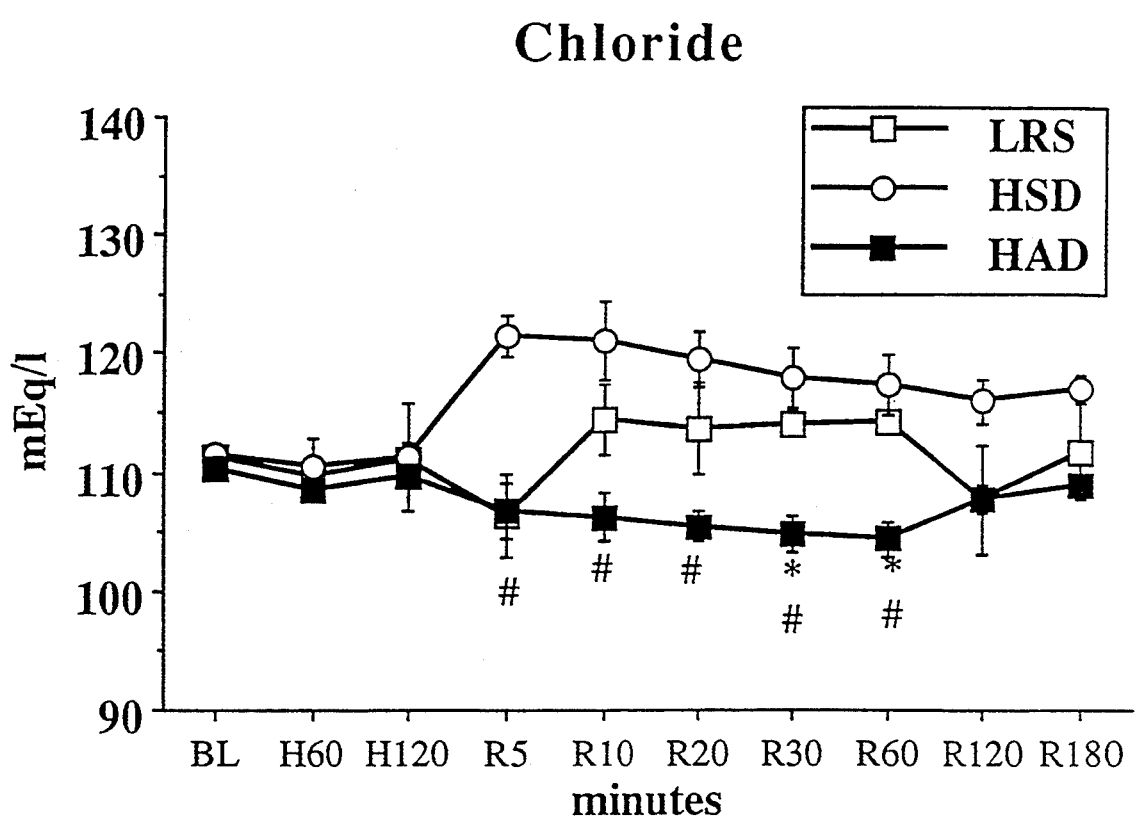
FIG. 5. Serum chloride transiently rose with the initial resuscitation phase in the HSD group while the other two groups did not exhibit this chloride elevation. Values represent the mean±SEM. *=$P<0.05$ LRS vs HAD; #=$P<0.05$ HSD vs HAD.

All three groups became mildly acidotic during hemorrhage (FIG. 4), with the pH ranging from 7.31 to 7.33. At 5 to 10 min. after resuscitation started, HSD group became more acidotic with a pH of 7.29 and 7.28 respectively and did not return to baseline until 30 min. post resuscitation. On the other hand, the HAD group's pH had normalized at 5 to 10 min and remained there during the full three hours of resuscitation. The acidosis of the LRS group did not worsen with resuscitation, however it did not normalize until after 60 min. Serum chloride transiently rose with the initial resuscitation phase in the HSD group while the other two groups did not exhibit this chloride elevation. (FIG. 5).

Figure 6:
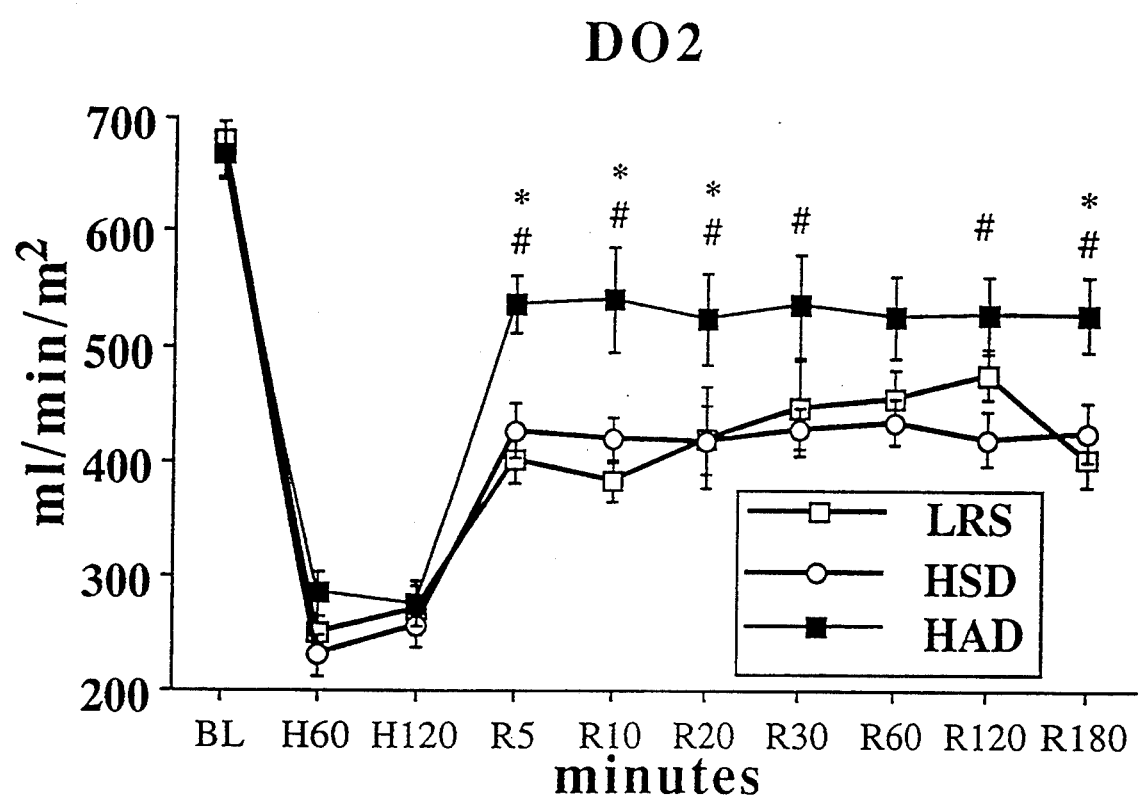
FIG. 6. The oxygen delivery ($DO_2$) during baseline, hemorrhage, and following resuscitation is shown. Values represent the mean±SEM. *=$P<0.05$ LRS vs HAD; #=$P<0.05$ HSD vs HAD.

The expected drop in oxygen delivery (DO$_2$) during hemorrhage to approximately 40% of baseline is shown in FIG. 6. There is no significant difference between the 3 groups. However, at 5 min of resuscitation DO$_2$ is significantly higher in HAD group than the other two groups and it remained significantly higher than the other two groups through the 3 hrs of resuscitation.

There is not significant difference in DO$_2$ between the HSD and the LRS group.

Figure 7:
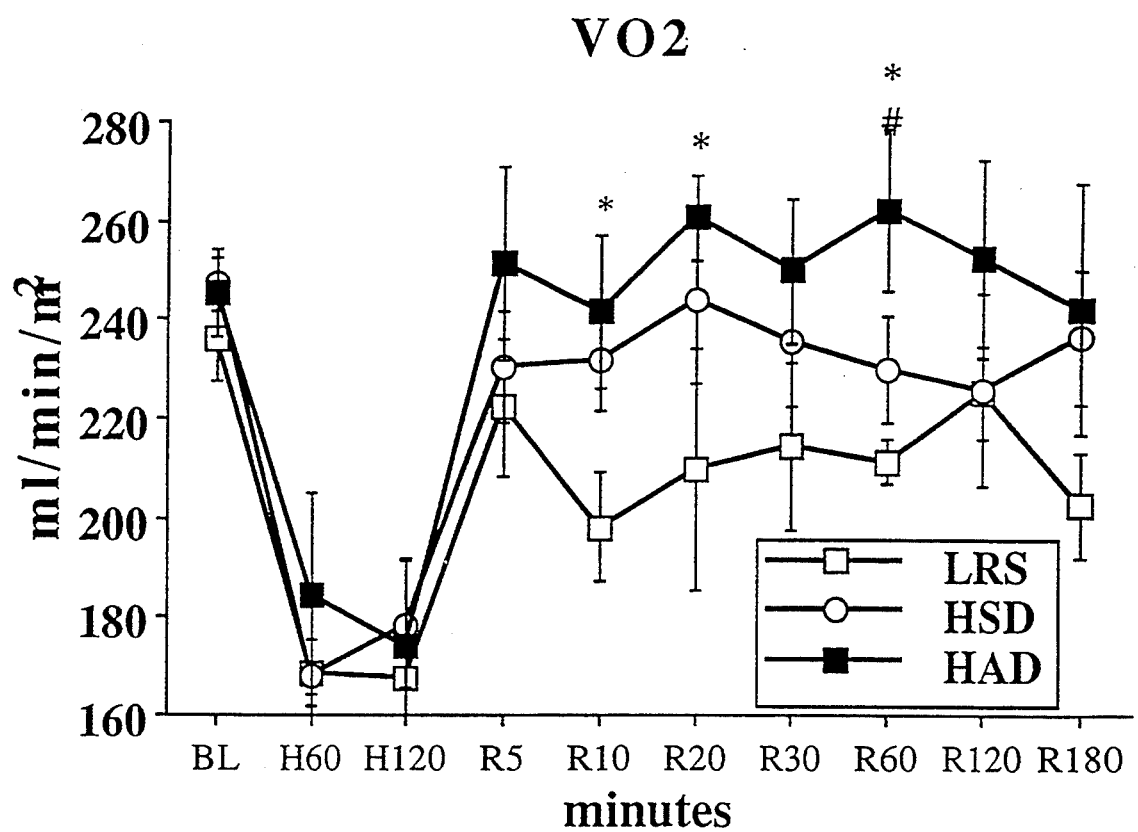
FIG. 7. The oxygen consumption ($VO_2$) during baseline, hemorrhage and following resuscitation is shown. Similar decreases in oxygen consumption in all groups during hemorrhage to 200 ml/min/m2 is seen. At resuscitation, oxygen consumption increased and returned and remained at baseline or above only in the HAD group. However, while $VO_2$ of HAD returned to baseline at 5 min and remained there throughout the 3 hrs of resuscitation, the increase of $VO_2$ of LRS was not sustained and became significantly lower than baseline at 10 min, 60 min and 180 min of resuscitation. The $VO_2$ of the HSD group increased and was sustained at an intermediate level between that of the HAD and LRS groups. Values represent the mean±SEM. *=$P<0.05$ LRS vs HAD; #=$P<0.05$ HSD vs HAD.
Figure 8:
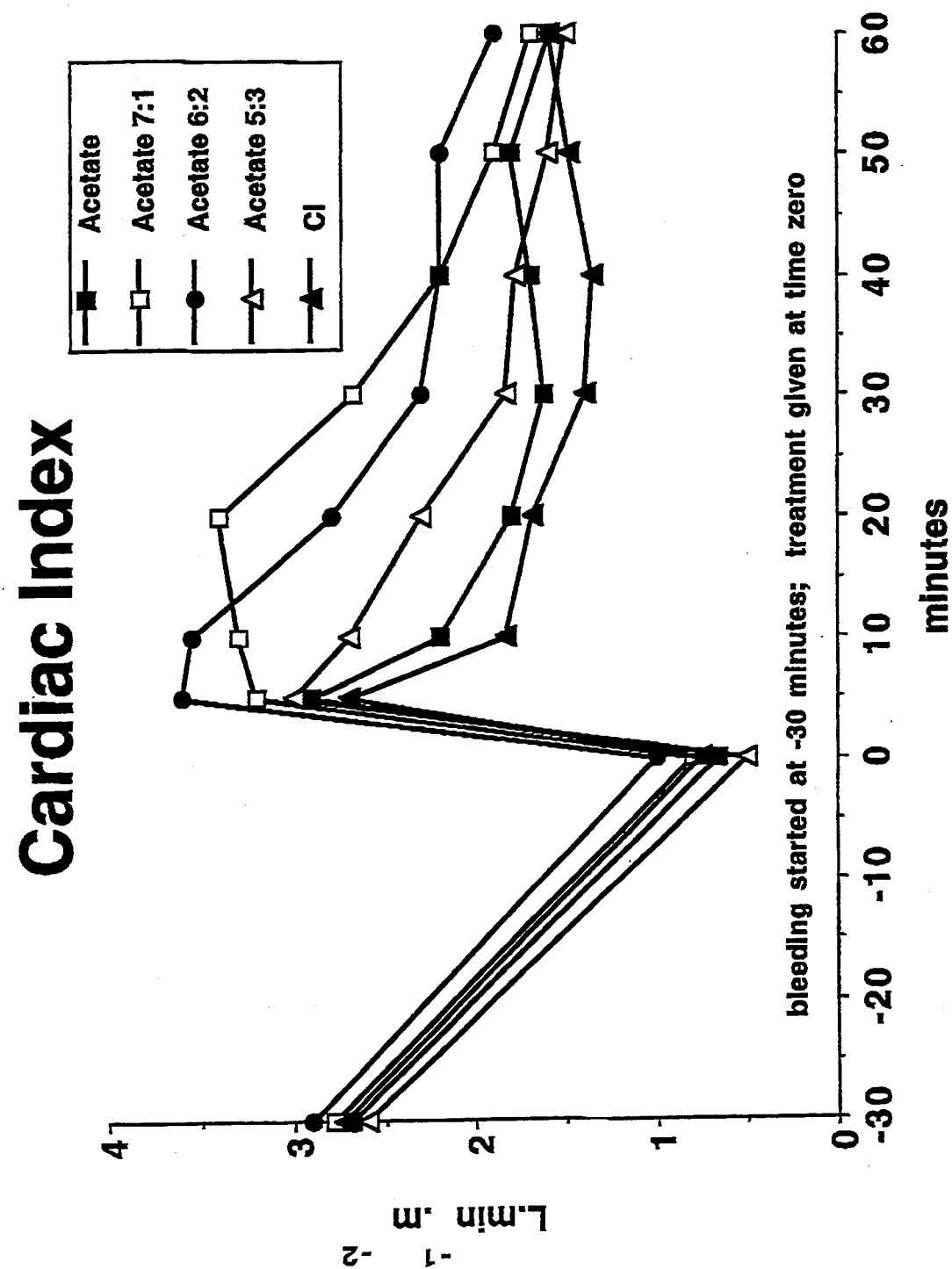
FIG. 8. Large increases of cardiac output after injection into anesthetized and hemorrhaged dogs of five different 2400 mOsm hypertonic Na acetate: Na chloride solutions each with 6% dextran70 is shown to occur with all the formulations. The acetate chloride combinations provided the highest and significantly more sustained responses with the 6:2, osmolar ratio providing the best response.

Similar decreases in oxygen consumption (VO$_2$) in all groups during hemorrhage period to 200 m/min/m$^2$ (approximately 75% of baseline) is shown in FIG. 7. At resuscitation, VO$_2$ increased and returned and remained at baseline or above in the HAD group. However while VO$_2$ of HAD returned above or to baseline at 5 min and remained there throughout the 3 hrs of resuscitation, the increase of VO$_2$ of LRS was not sustained and became significantly lower than baseline at 10 min, 60 min and 180 3 min of resuscitation. The VO$_2$ of the HSD group was intermediate between the other two groups.

Hemoglobin of each group at baseline, during hemorrhage and resuscitation is shown in Table 1. Hemoglobin levels were not significantly different in the three groups until initiation of resuscitation. Thereafter, the blood hemoglobin is significantly higher in the HAD group than the other two groups.

TABLE 1

Blood hemoglobin levels (g/100 mL) at baseline, 120 minutes hemorrhage, and 5, 10, 30, and 180 minute resuscitation

|  | Base | Hemorr 120 min | Resus 5 min | Resus 10 min | Resus 30 min | Resus 180 min |
|---|---|---|---|---|---|---|
| LRS | 8.9 ±0.1 | 8.8 ±0.6 | 6.1 ±0.2 | 6.0 ±0.2 | 5.7 ±0.3 | 5.8 ±0.3 |
| HSD | 8.7 ±0.2 | 8.1 ±0.4 | 6.6 ±0.3 | 6.1 ±0.2 | 5.4 ±0.4 | 5.5 ±0.4 |
| HAD | 8.7 ±0.2 | 8.1 ±0.6 | 6.7* ±0.3 | 6.5* ±0.2 | 6.4* 0.3# | 6.2# ±0.3 |

In Table 2, oxygen saturation during baseline, hemorrhage and following resuscitation is shown. There are no differences in the three groups until resuscitation when oxygen saturation is significantly higher in the HAD group than the other two groups. This difference, together with the higher hemoglobin levels, accounts for the significantly higher DO$_2$ in HAD than the other two groups.

TABLE 2

Percent arterial oxygen saturation (SaO$_2$) of blood at baseline, 120 minutes hemorrhage, and 5, 10, 30, and 180 minute resuscitation

|  | BL | Hemorr 120 min | Resus 5 min | Resus 10 min | Resus 30 min | Resus 180 min |
|---|---|---|---|---|---|---|
| LRS | 91.6 ±0.3 | 91.9 ±0.6 | 92.1 ±0.3 | 92.3 ±0.4 | 92.1 ±0.5 | 92.6 ±0.6 |
| HSD | 92.1 ±0.3 | 92.1 ±0.2 | 91.7 ±0.6 | 91.8 ±0.4 | 92.4 ±0.5 | 93.1 ±0.6 |
| HAD | 92.1 ±0.2 | 92.3 ±0.6 | 93.3* ±0.6# | 93.1# ±0.5 | 93.2* ±0.3 | 93.1 ±0.7 |

Data showed that all three groups became mildly acidotic during hemorrhage period; however, the pH in the HAD group rapidly normalized with resuscitation. In the HSD group there was an initial hyperchloremic acidosis which was not seen in the HAD group because of replacement of the chloride with the buffer capacity of acetate. An initial hyperchloremic acidosis was seen also with HSD resuscitation in human trials which worsened the metabolic acidosis of hemorrhagic shock. The pH in LRS group also normalized but more slowly and not until 20-30 min after resuscitation initiated probably due to continued inadequate oxygen delivery after the initial LRS resuscitation.

EXAMPLE 2

Effect of Different Chloride/Acetate Ratio on Plasma Electrolytes

Experiments were conducted to show the effect of hypertonic formulations of various ratios of sodium chloride and sodium acetate on plasma sodium ions and chloride.

A pig was anesthetized with isoflurane. Vascular cannulas were placed in the aorta and vena cava and a thermodilution catheter placed in the pulmonary artery for hemodynamic monitoring. After a mild hemorrhage, the pig was infused with 4 ml/kg of 2400 mOsm of a 1:7 mixture of NaCl and NaAc. Blood samples were taken and hemodynamics measured. In subsequent 30 min periods, 4 ml/kg 2400 mOsm solutions of 2:6, 3:5 and 4:4 osmolar parts NaCl/NaAc were infused. Isochloremic resuscitation occurred with the 2:6 NaCl/NaAc mixture. The greatest augmentation of blood flow was shown with the 2:6 formulation.

EXAMPLE 3

Comparison of Hyperosmotic Chloride/Acetate with Standard Resuscitation Fluids in Managing Uncontrolled Bleeding The objective of the experiment was to determine the effect of using hyperosmotic sodium chloride: sodium acetate solutions on cardiovascular function in circumstances mimicking an average emergency rescue of patients undergoing intense blood loss.

Experiments were performed on dogs in controlled laboratory conditions designed to emulate the course of severe arterial bleeding as it may occur after a large artery or arteries are lesioned in trauma. In such a situation it is presumed that prehospital care, once it reaches the patient, is able to deliver resuscitative treatment but unable to interrupt the internal blood loss. The concept of arterial bleeding presumes (i) that there is an initial, predetermined rate of blood loss, which represents the dimension of the arterial lesion, and (ii) that blood will be lost at a variable rate which remains proportional to prevailing arterial pressure.

The initial bleeding rate was arbitrarily established at 25 ml/min, equivalent to a bleeding rate of 100 ml/min for a normal 70 kg human adult. Once started, bleeding was never interrupted, for a total duration of 90 min. Various alternative treatments were instituted at 30 min in different dogs.

In a typical experiment, there were four groups of dogs: a 1st group was left untreated (NT); a 2nd group received the standard of care treatment consisting of a continuous infusion of 24 ml/min of crystalloid solution, from 30 to 90 min. (ST); a 3rd group received the same treatment as the ST group, but a rapid infusion of 6 ml/kg of hyperosmotic hyperoncotic NaCl (7.5%)+dextran70 (6%) was given at the beginning of treatment (HSD); a 4th group received the same as the ST group, but a rapid infusion of 6 ml/kg of 2 molar parts NaCl and 6 molar parts of NaAc plus dextran was given at the beginning of resuscitation (HAD). All groups were homogeneous in all respects before treatment.

The NT group declined progressively to critically low levels of arterial pressure, cardiac output, oxygen availability, and oxygen consumption, even though the blood loss incurred was the smallest of all groups. This smaller blood loss was a necessary consequence of the experimental concept. 90% of all dogs in this group died within the experimentation period. Deaths occurred between 40 and 90 min after the start of bleeding.

The ST group exhibited a gradual recovery of arterial pressure, cardiac output, oxygen availability and oxygen consumption, once the standard of care treatment was instituted.

The addition of HSD at the start of treatment (HSD group) elevated arterial pressure and cardiac output, in comparison to the ST group, but failed to clearly improve oxygen consumption, even though the oxygen availability was higher than that observed in the ST group.

The addition of the HAD fluid at the start of treatment did not significantly alter blood pressure by comparison with the ST group, but cardiac output, oxygen availability and oxygen consumption were much higher than observed in the other test groups. Unexpectedly, in the HAD group, oxygen consumption recovered to essentially normal levels after approximately 30 minutes. Arterial pH dropped in the HSD group, but remained stable in the HAD group. The chloride level rose in the HSD group, but remained stable in the HAD group.

EXAMPLE 4

Three groups of dogs were used as models for hypovolemia from severe arterial bleeding. Bleeding rates were established as in Example 2. One group of dogs received no treatment (NT); a second group received HSD alone, that is, a rapid infusion of 6 ml/kg of hyperosmotic/hyperoncotic NaCl (7.5%) plus dextran70 (6%) given at the beginning of treatment (HSD) and the last group received a hypertonic solution of 6 ml/kg of 2:6 osmolar parts of sodium chloride:sodium acetate, 2400 mOsm total (HAD).

HSD alone and HAD alone induced higher levels of arterial pressure, cardiac output and oxygen availability, in comparison with the NT group, but HAD induced a greater and longer lasting recovery of oxygen consumption.

EXAMPLE 5

Comparative Resuscitation Treatments of Acetate, Chloride and Combination Acetate/Chloride Formulations In a protocol of controlled hemorrhage, different ratios of hypertonic sodium chloride and sodium acetate were compared for efficacy in a double-blind study. FIGS. 8 to 12 represent the variation of several physiologies parameters within 60 min of the injection.

Twenty splenectomized dogs (average weight 16.5 kg) anesthetized with morphine and pentobarbital were bled over 30 min. Pretreatment parameters (no difference between groups) were: blood loss 41.2 mL/kg; MAP: 52.9mm Hg; cardiac index: 0.79 L/min per m$^2$. Blood removal was then interrupted and each dog treated with a single injection of 4 ml/kg of one of the following solutions. All solutions were 2400 mosm/L salt solutions in 6% lactate. Pretreatment parameters (no difference between groups) were: blood loss: 41.2 ml/kg; MAP: 52.9 mm Hg; Cardiac index: 0.79 L min$^{-1}$ m$^{-2}$. The five solutions, see Table 3, were: acetate: 2400 mOsm Na acetate in 6% dextran70; chloride: 2400 mOsm/L NaCl in 6% dextran70; acetate 7:1 (seven osmolar parts Na acetate to one osmolar part Na chloride in 6% dextran70); acetate 6:2; and acetate 5:3.

TABLE 3

| Salt | Ratio | % NaCl | % NaAc |
|---|---|---|---|
| NaAc | 8:0 | 0 | 10.7 |
| NaAc/NaCl | 7:1 | 0.9 | 9.4 |

TABLE 3-continued

| Salt | Ratio | % NaCl | % NaAc |
|---|---|---|---|
| NaAc/NaCl | 6:2 | 1.8 | 8.0 |
| NaAc/NaCl | 5:3 | 2.7 | 6.7 |
| NaCl | 0.8 | 7.5 | 0 |

All solutions were 6% in dextran and 2400 mOsm/L

Figure 9:
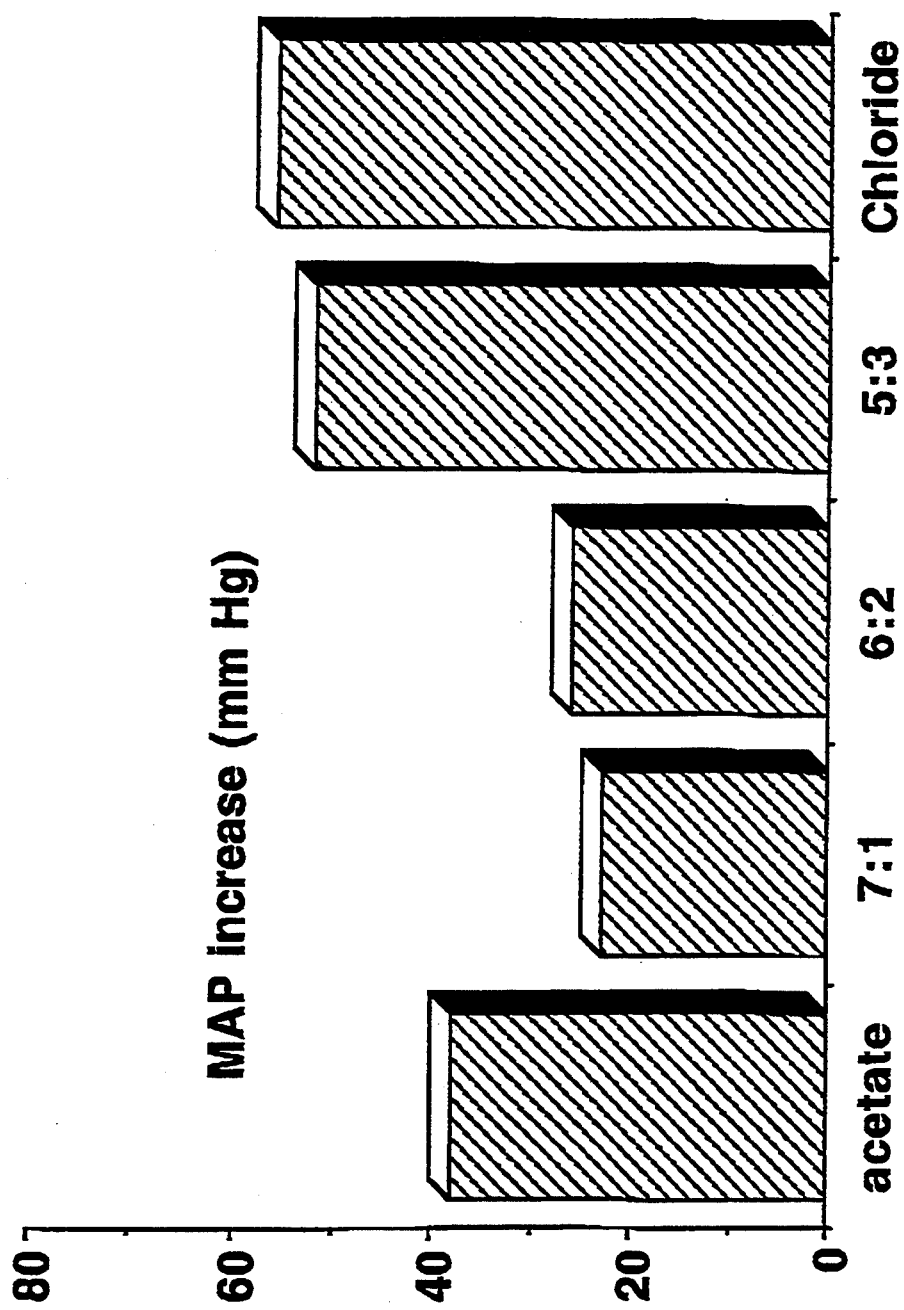
FIG. 9. The increase in mean arterial pressure after injection into anesthetized and hemorrhaged dogs of five different 2400 mOsm hypertonic Na acetate: Na chloride solutions each with 6% dextran70 is shown. Minimal increases in arterial pressure occurred only with the 7:1 and 6:2 osmolar ratio solutions with the 7:1 having the smallest increase.
Figure 10:
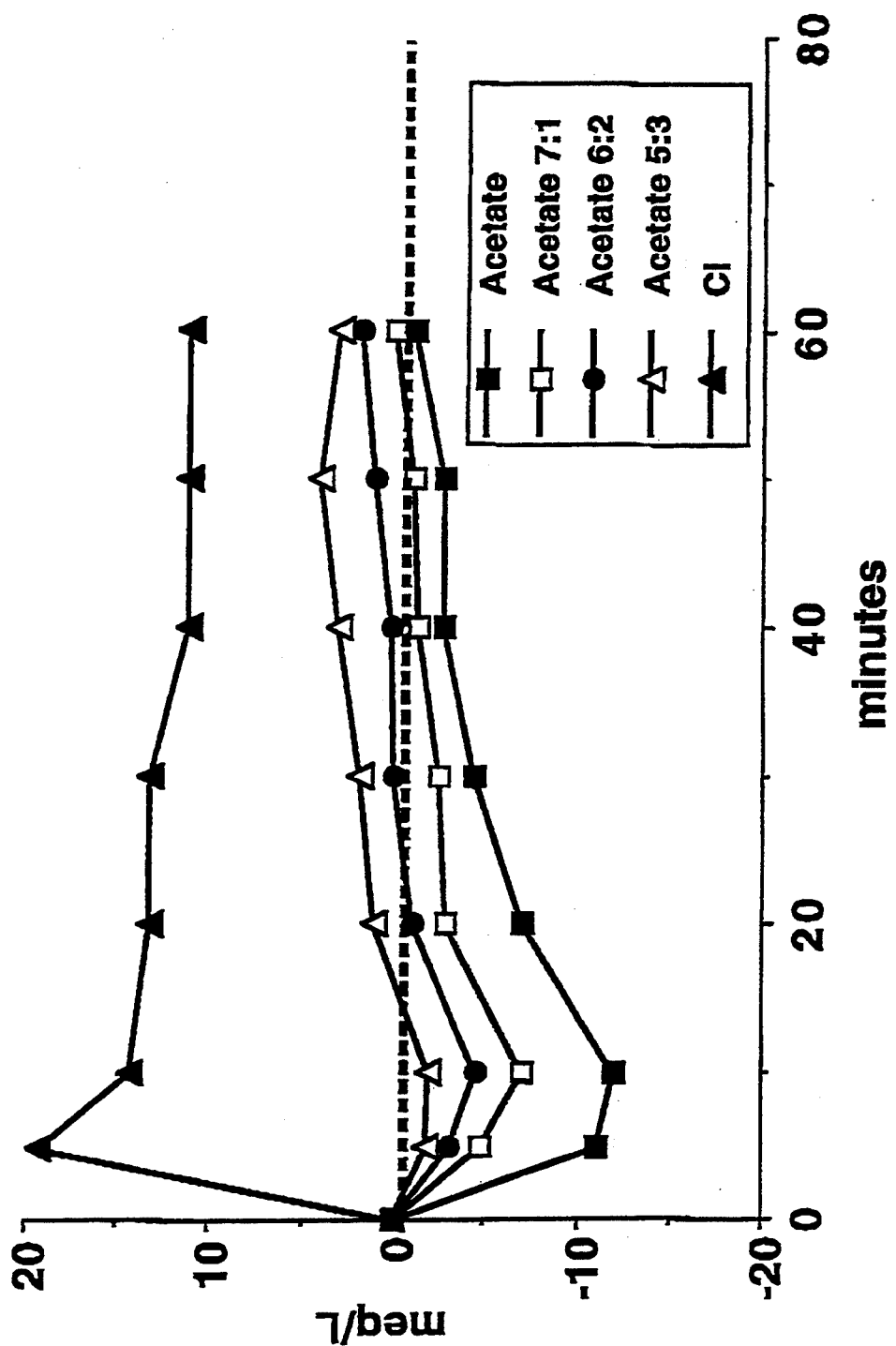
FIG. 10. Changes in the serum concentrate of chloride after injection into anesthetized and hemorrhaged dogs of five different 2400 mosm hypertonic Na acetate: Na chloride solutions each with 6% dextran 70 is shown. Only the solutions with the 7:1, 6:2, and 5:3 osmolar ratios of acetate to chloride provide isochloremia conditions with 5:3 and 6:2 being the most isochloremic.
Figure 11:
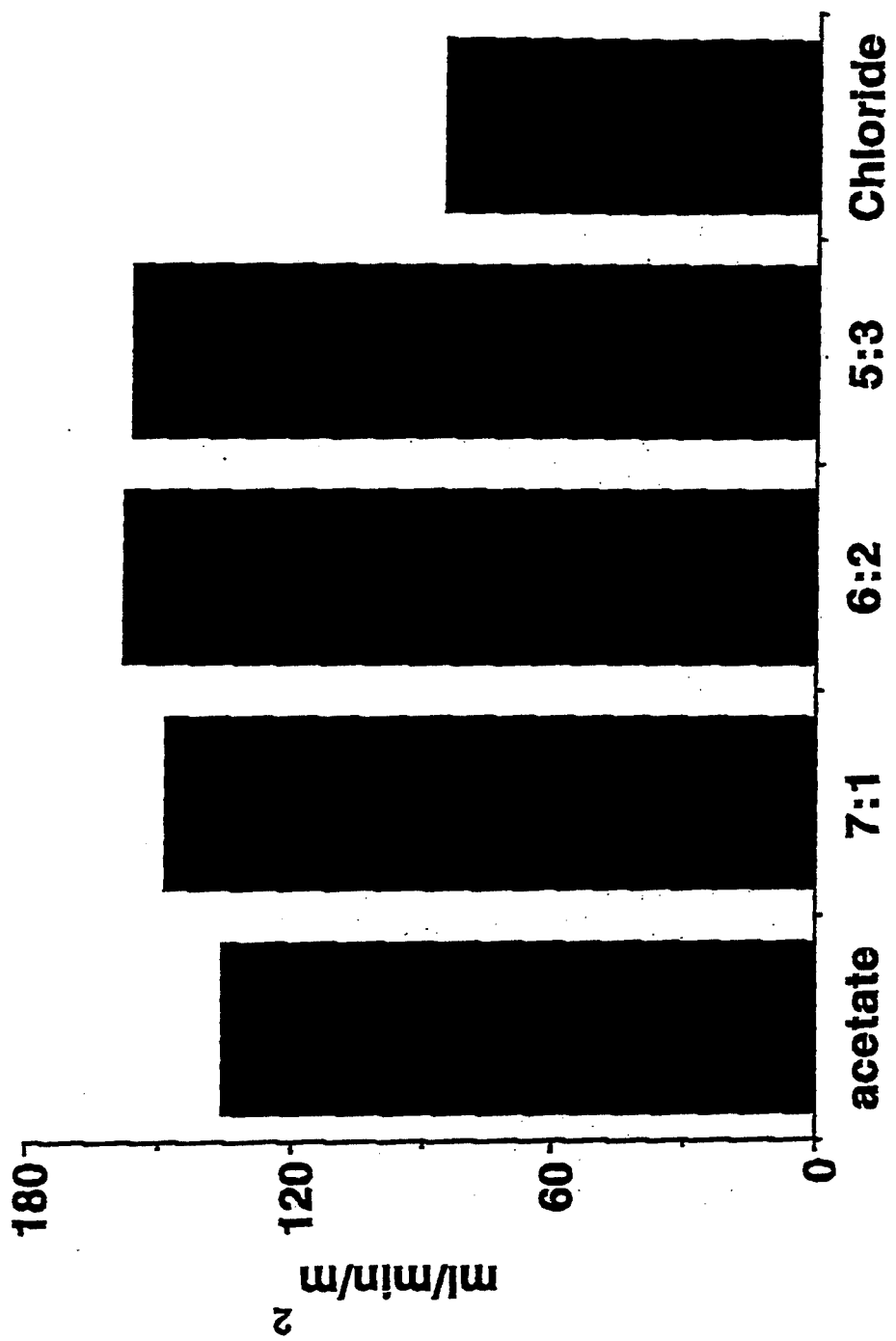
FIG. 11. The increase in oxygen consumption was shown to be best achieved with the Na acetate: Na chloride formulations with best response from the 6:2 ratio.
Figure 12:
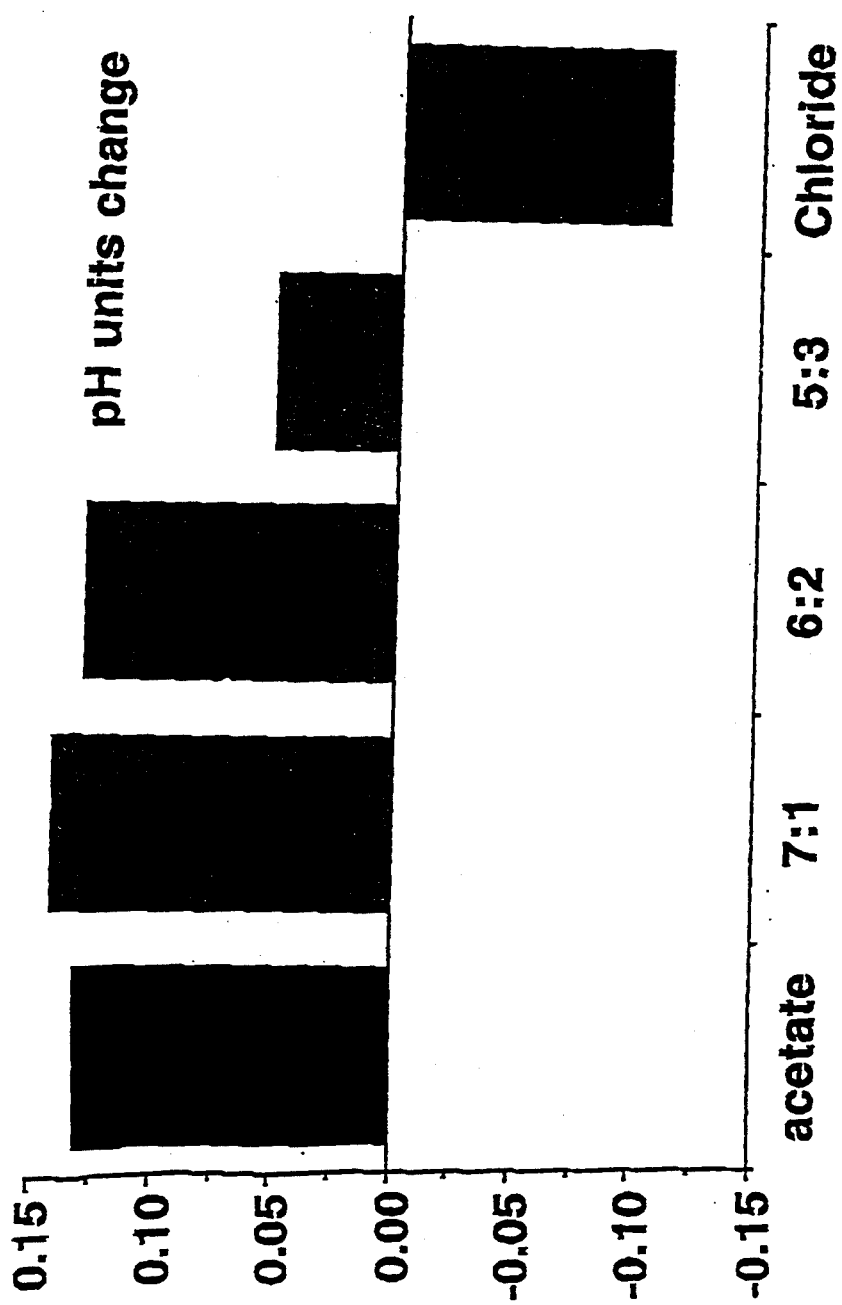
FIG. 12. Hypertonic NaCl was shown to cause an acidosis. The most isochloremic formulation was the 5:3 preparation which also caused the smallest initial increase in pH. All the acetate solutions increased pH, which is considered a beneficial effect in treating shock.

The maximal variation of mean arterial pressure, cardiac output, oxygen consumption, plasma sodium, plasma chloride, arterial pH and base excess within 60 min of the injection was determined. Acetate 6:2 induced maximal increase of cardiac index (FIG. 8) and $VO_2$ (FIG. 11), while only acetate 7:1 and 6:2 produced minimal increases in MAP (FIG. 9). Acetate 6:2 was more nearly isochloremic than 7:1 (FIG. 10). Considering all measured parameters, 6:2 was marginally better than 7:1 and even 5:3 offers some of the effectiveness of this formulation. These data show that the effects observed in the dog models regarding oxygen consumption were a consequence of the new formulation with hyperosmotic sodium chloride:sodium acetate in the specified range. Because the dextran concentration was the same in all groups, it is unlikely that dextran contributed to the differences in effectiveness.

EXAMPLE 6

Comparison of Minimal Infusions as Needed of Hyperosmotic Sodium Chloride and Acetate Dextran with Isotonic Fluid and Hypertonic Saline Dextran in Uncontrolled Hemorrhage Anesthetized pigs with severe hemorrhage and aortotomy were employed to determine the volume of hyperosmotic/hyperoncotic resuscitation fluid required to restore cardiac index to 60% of baseline value for 20 min. The period of time was chosen to simulate a typical time period required from the time of severe trauma to reach hospital facilities. The value of 60% of baseline cardiac output is sufficient to sustain reasonable metabolic function. Such might be the case for example in ambulance transport within the suburban area of a large city or transport time by helicopter from a more rural outlying area.

Anesthetized pigs were used as models for severe hemorrhage and aortotomy employing surgical procedures previously described. 10 pigs were divided into three groups and infused with one of the following formulations: HAD which comprises 6% dextran70 and a sodium acetate:chloride ratio of 6:2; HSD which comprised 6% dextran70 and 7.5% sodium chloride; and LRS which was isotonic lactated Ringers. Table 5 shows the volumes required for each solution to restore the cardiac index to 60% of its baseline value over a 20 min period up to a maximum of 10 mL/kg. This maximum volume represents 700 mL in a typical patient and corresponds to a typical volume administered through small bone catheters by paramedics during a 20 min ambulance transport.

TABLE 4

| Solution | No. animals | mL/kg |
|---|---|---|
| HSD | 3 | 5.33 ± 1.8 |
| HAD | 3 | 2.0 ± 0.6 |
| LRS | 4 | 8.8 ± 1.3 |

The data show that the 2400 mOsm solutions require only relatively small volumes to rapidly restore cardiac index and that the combined acetate/chloride formulation requires significantly less volume than formulations with chloride or acetate.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, additional components added to the sodium chloride/sodium acetate solution may be used to modify properties of the fluid for special applications. Other crystalloids such as salts with buffering capacity, cations such as potassium or magnesium, antishock drugs and the like may be included. These and obvious related modifications are contemplated to be within the scope of the claims.

REFERENCES

The references listed below are incorporated herein by reference to the extent that they supplement, explain, provide a background for or teach methodology, techniques and/or compositions employed herein.

Bickell, W., Bruttig, S., Millnamow, G. O'Benar, J., and Wade, C., The detrimental effects of intravenous crystalloid after aortotomy in swine, *Surgery*, 110:529-536, 1991.

Bickell, W. H., Bruttig, S. P., and Wade, C. E., Hemodynamic response to abdominal aortotomy in the anesthetized swine, *Circ. Shock*, 28:321-332, 1989.

Bitterman, H., Triolo, J., and Lefer, A. M. Use of hypertonic saline in the treatment of hemorrhagic shock, *Circ. Shock*, 21:271-283, 1987.

Cone, J. B., Wallace, B. H., Caldwell, F. T., Jr., Smith, S. D. and Searcey, R., Am. J. Surg. 154, 585-588 (1987).

Fox, C. L., Jr., U.S. Pat. No. 3,993,750, Nov. 23, 1976.

Gazitua, S., Scott, J. B., Swindall, B., and Haddy, F. J. Resistance responses to local changes in plasma osmolality in three vascular beds, *Amer. J. Physiol.*, 220(2):384-391, 1971.

Guyton, A. C., Regulation of Acid-Base Balance. In: Textbook of Medical Physiology. Eight Edition. Philadelphia: Saunders; 1991, 332-33.

Guyton, A. C., Transport of Oxygen and Carbon Dioxide in the Blood and Body Fluids. In: Textbook of Medical Physiology. Eighth Edition. Philadelphia: Saunders; 1991, 436-37.

Gross, D., Landau, E., Assalia, A., and Krausz, M., Is hypertonic saline resuscitation safe in 'uncontrolled' hemorrhagic shock?, *J. Trauma*, 28:751-756, 1988.

Kien, N. D., and Kramer, G. C. Cardiac performance following hypertonic saline, *Braz. J. Med. Biol. Res.*, 22:245-248, 1989.

Kramer, G. C., English, T. P., Gunther, R. A., and Hocroft, J. W., Physiological mechanisms of fluid resuscitation with hyperosmotic/hyperoncotic solutions. In Passmore J. C. (ed): "Perspectives in Shock Research," *Progress in Clinical and Biological Research*, pp: 331-320, 1989.

Kramer, G. C. and Holcroft, J. W., U.S. Pat. No. 4,908,350, Mar. 13, 1990.

Kramer, G. C. and Perron, P. R., U.S. Pat. No. 4,927,806, May 22, 1990.

Kramer, G. C., Perron, P., Lindsey, D. C., Ho, H. S., Gunther, R. A., Boyle, W. A., and Holcroft, J. W., Small volume resuscitation with hypertonic saline dextran solution, *Surgery* 100:239–246.

Kreimeir, U., Bruckner, U. B., Schoenberg, M., Scmidt, J., and Messmer, K. Hypertonic saline dextran solution for resuscitation after hemorrhagic hypotension, *Circ. Shock*, 21:377, 1987.

Lopes, O. U., Pontiere, V., Rocha e Silva, M., Jr., and Lopes, O. V., Hyperosmotic NaCl and severe hemorrhagic shock, *Am. J. Physiol.*, 241:H883-H890, 1981.

Lopes, O. U., Velasco, I. T., Guertzenstein, P. G., Rocha e Silva, M., Jr., and Pontieri, V. Hypertonic sodium chloride restores mean circulatory filling pressure in severely hypovolemic dogs, *Hypertension*, 81(1): 195–199, 1986.

Maningas, P. A., Resuscitation with 7.5% NaCl in 6% dextran-70 during hemorrhagic shock in swine: effects on organ blood flow, *Crit. Care Med.*, 15:1121-1126, 1987.

Maningas, P. A., DeGuzman, L. R., Tillman, F. J., Hinson, C. S., Priegnitz, K. J., Volk, K. A., and Bellamy, R. F., Small volume infusion of 7.5% NaCl in 6% dextran 70 for the treatment of severe hemorrhagic shock in swine, *Ann. Emerg. Med.*, 15:1131-1137, 1986.

Mattox, K. L., Maningas, P. A., Moore, E. E., et al., Pre-hospital hypertonic saline/dextran infusion for post-traumatic hypotension. The U.S.A. Multicenter Trial, *Ann. Surg.*, 213:482-491, 1991.

Mattox, K., Martin, R., Wall, M., Pepe, P., and Bickell, W. Deliberate fluid restriction in post traumatic hypovolemic hypotension, *Proceedings of the Fifth International Conference on Hypertonic Resuscitation*, Galveston, Tex., Jun. 3–5, 1992.

Monafo, W. W., Chuntrasakul, C., and Ayvazian, V. H., Hypertonic sodium solutions in the treatment of burn shock, *Amer. J. Surg.*, 126:78, 1973.

Moylan, J. A., Jr., Recker, J. M., and Mason, A. D., Resuscitation with hypertonic lactated saline in thermal injury. *Amer. J. Surg.*, 125:580, 1973.

Muir, W. W., and Sally, J. Small volumes resuscitation with hypertonic saline solution in hypovolemic cats, *Am. J. Vet. Res.*, 50:1883-1887, 1989.

Nakayama, S., Sibley, L., Gunther, R. A., Holcroft, J. W., and Kramer, G. C. Small volume resuscitation with hypertonic saline, *Surgery*, 100:239-246, 1986.

Onarheim, H., Missavage, A. E., Kramer, G. C., and Gunther, R. A. Effectiveness of hypertonic saline-dextran 70 for initial fluid resuscitation of major burns, *J. Trauma*, 30:597-603, 1990.

Rocha e Silva, M., Velasco, I. T., Silia, R. R. et al., Am. J. Physiol. 253H 751 (1987).

Rocha e Silva, M., Jr., Negraes, G. A., Soares, A. M., Pontieri, V., and Loppnow, L., Hypertonic resuscitation from severe hemorrhagic shock: Patterns of regional circulation, *Circ. Shock*, 19:165-175, 1986.

Rosen, A. I., Gould, S. A., Sehgal, L. R., et al. Hemoglobin solutions as red cell substitutes, *Crit Care Med*, 10:275-78, 1982.

Silbert, S., The treatment of thromboangitis obliterans by intravenous injection of hypertonic salt solution: Preliminary report, *J. Amer. Med. Assoc.* 86:1759, 1926.

Smith, G. J., Kramer, G. C., Perron, P., Nakayama, S., Gunther, R. A., and Holcroft, J. W., A comparison of several hypertonic solutions for resuscitation of bled sheep, *J. Surg. Res.*, 39:517-528, 1985.

Smith, J. P., Bodai, B. I., and Hill, A. S. Pre-hospital stabilization of critically injured patients: a failed concepts, *J. Trauma*, 25:65-70, 1985.

Vassar, M., Perry, C., and Holcroft, J. Analysis of potential risks associated with 7.5% sodium chloride resuscitation f traumatic shock, *Arch. Surg.*, 125:1309-1315, 1990.

Velasco, I. T., Oliveira, M. A., Oliveira, M. A., Rocha e Silva, M. Circ. Shock 21, 338–343 (1987).

Velasco, I. T., Pontieri, V., Rocha e Silva, Jr., M., and Lopes, O. V., Hypertonic NaCl and severe hemorrhagic shock, *Am. J. Physiol.*, 239:H664-H673, 1980.

Velasco, I. T., Rocha e Siva, M., Oliveira, M. A., Oliveira, M. A., and Silva, R. I. N., Hypertonic and hyperoncotic resuscitation from severe hemorrhagic shock in dogs: a comparative study, *Crit. Care Med.*, 17(3):261-264, 1989.

Wade, C. E., Hannon, J. P., Bossone, C. A., and Hum, M. M., Superiority of hypertonic saline/dextran over hypertonic saline during the first 30 min. of resuscitation following hemorrhagic hypotension in conscious swine, *Resuscitation*, 20:49-56, 1990.

Walsch, J. C., and Kramer, G. C., Resuscitation of hypovolemic sheep with hypertonic saline/dextran: the role of dextran, *Circ. Shock*, 34(3):336-343, 1991.

Wildenthal, K., Mierzwiak, D. S., and Mitchell, J. H. Acute effects of increased serum osmolality on left ventricular performance, *Am. J. Physiol.*, 216(4):898-904, 1969.

What is claimed is:

1. An isochloremic pharmaceutical composition for improving oxygen delivery and oxygen consumption in an individual in need of fluid resuscitation consisting essentially of about 2 molar parts of sodium chloride and about 6 molar parts of sodium acetate in a solution having a total osmolarity of at least 500 mOsm.

2. An isochloremic pharmaceutical composition for improving oxygen delivery and oxygen consumption in an individual in need of fluid resuscitation consisting essentially of about 1 molar part of sodium chloride and about 7 molar parts of sodium acetate in a solution having a total osmolarity of at least 500 mOsm.

3. An isochloremic pharmaceutical composition for improving oxygen delivery and oxygen consumption in an individual in need of fluid resuscitation consisting essentially of about 3 molar parts of sodium chloride and about 5 molar parts of sodium acetate in a solution having a total osmolarity of at least 500 mOsm.

4. An isochloremic pharmaceutical composition for improving oxygen delivery and oxygen consumption in an individual in need of fluid resuscitation consisting essentially of about 2 molar parts of sodium chloride and about 6 parts of sodium acetate and a dextran in a solution having a total osmolarity of at least 500 mOsm.

5. The isochloremic pharmaceutical composition of claim 4 wherein the dextran is about 4% to about 8% by weight.

6. The isochloremic hypertonic pharmaceutical composition of claim 1 or claim 2 or claim 3 wherein the total osmolar concentration is at least 1000 mOsm/liter.

7. The isochloremic hypertonic pharmaceutical composition of claim 1 or claim 2 or claim 3 wherein the total osmolar concentration is about 2400 mOsm/liter.

8. An isochloremic pharmaceutical composition for improving oxygen delivery and oxygen consumption in an individual in need of fluid resuscitation consisting essentially of about 2 molar parts of sodium chloride, about 6 molar parts of sodium acetate, and a colloid selected from the group consisting of soluble starch, gelatin, metal salt, an amino acid and protein.

9. The isochloremic pharmaceutical composition of claim 8 wherein the protein is albumin or stroma-free hemoglobin.

10. The isochloremic pharmaceutical composition of claim 8 wherein the soluble starch is hydroxyethyl starch.

11. The isochloremic pharmaceutical composition of claim 8 wherein the soluble starch is pentastarch or pentastarch fraction.

12. A method of improving oxygen delivery and consumption in an individual suffering hemorrhagic shock, comprising administration to said individual of a therapeutically effective amount of a pharmaceutical composition consisting essentially of about 2 molar parts of sodium chloride and about 6 molar parts of sodium acetate or about 1 molar part of sodium chloride and about 7 molar parts of sodium acetate or about 3 molar parts of sodium chloride and about 5 molar parts of sodium acetate in a solution having a total osmolarity of at least 500 mOsm.

13. A method of improving oxygen delivery and consumption in an individual suffering hemorrhagic shock, comprising administration to said individual of a therapeutically effective amount of a pharmaceutical composition consisting essentially of about 2 molar pans of sodium chloride and about 6 molar pans of sodium acetate or about 1 molar part of sodium chloride and about 7 molar parts of sodium acetate or about 3 molar parts of sodium chloride and about 5 molar pans of sodium acetate and a dextran in a solution having a total osmolarity of at least 500 mOsm.

14. The method of claim 12 wherein the effective amount administered is about 3 to about 5 ml/kg.

15. The method of claim 12 wherein the administration is over a period of about 3 hours.

16. The method of claim 12 wherein the individual is in circulatory shock or at risk for circulatory shock.

17. The method of claim 16 wherein the circulatory shock is from burn, hemorrhage, sepsis, allergic reaction or heart failure.

18. The method of claim 12 wherein administration is by intravascular infusion into soft tissue vessels or bone marrow.

19. The method of claim 12 wherein the total osmolar concentration is about 2400 mOsm.

20. The method of claim 13 wherein the dextran is about 4% to about 8% by weight.

21. A prepackaged resuscitation composition comprising the composition of claim 1, claim 2 or claim 3 which is sterilely disposed in a container suitable for administration to a subject in need of said resuscitation composition.

22. The prepackaged resuscitation composition of claim 21 wherein the container is pressurized or provided with a pump to provide automatic delivery when suitably set up for administration.

23. The prepackaged resuscitation composition of claim 21 wherein the container is a plastic bag.

24. The prepackaged resuscitation composition of claim 21 which further includes suitable intravenous access paraphernalia.

25. The prepackaged resuscitation composition of claim 21 which further includes intraosseous access paraphernalia.

* * * * *

UNITED STATES PATENT AND TRADEMARK OFFICE

CERTIFICATE OF CORRECTION

PATENT NO. : 5,443,848

DATED : August 22, 1995

INVENTOR(S) : George C. Kramer, Mauricio Rocha-e-Silva, Irineu T. Velasco and Charles E. Wade It is certified that error appears in the above-identified patent and that said Letters Patent is hereby corrected as shown below:

```
In claim 13, column 21, line 27 and line 28, delete "pans" and
insert --parts--.
```

Signed and Sealed this

Twenty-fourth Day of October, 1995

Attest:

BRUCE LEHMAN

Attesting Officer

Commissioner of Patents and Trademarks